(12) United States Patent
Frade

(10) Patent No.: US 6,818,744 B1
(45) Date of Patent: Nov. 16, 2004

(54) P53 REGULATORY PROTEIN CALLED RB18A AND USES THEREOF

(76) Inventor: Raymond Frade, 69 avenue du Général Leclerc, Paris (FR), 75014

(*) Notice: Subject to any disclaimer, the term of this patent is extended or adjusted under 35 U.S.C. 154(b) by 0 days.

(21) Appl. No.: 09/581,472

(22) PCT Filed: Dec. 14, 1998

(86) PCT No.: PCT/EP98/08560

§ 371 (c)(1),
(2), (4) Date: Aug. 14, 2000

(87) PCT Pub. No.: WO99/31231

PCT Pub. Date: Jun. 24, 1999

(30) Foreign Application Priority Data

Dec. 15, 1997 (EP) .............................. 97403051

(51) Int. Cl.$^7$ ................................. C07K 1/00
(52) U.S. Cl. ...................... 530/350; 530/300; 530/324; 514/12
(58) Field of Search ................ 530/350, 300, 530/324; 514/12

(56) References Cited

U.S. PATENT DOCUMENTS 6,248,520 B1 * 6/2001 Roeder et al. ................. 435/6

OTHER PUBLICATIONS

Zhu et al J. Biol. Chem vol. 272 p. 2550 (10/97).*
Skolnick et al TIBTECH vol. 10 p. 34 (1/00).*
Barel et al, J. Allergy and Clinical Immunology vol. 99 p. S33 (Jan. 1997).*
FRade et al Oncogene vol. 21 p. 861 (2002).*

* cited by examiner

Primary Examiner—Sheela Huff
(74) Attorney, Agent, or Firm—Larson & Taylor PLC

(57) ABSTRACT

This invention relates to a new protein called RB18A for "Recognized By PAb18O1 moAntibody", which is a p53 regulatory protein, to the nucleotide sequence encoding said protein, and to the diagnostic and therapeutic applications thereof, in particular for the diagnosis, prevention or treatment of neoplasia.

3 Claims, 17 Drawing Sheets

Figure 2A:
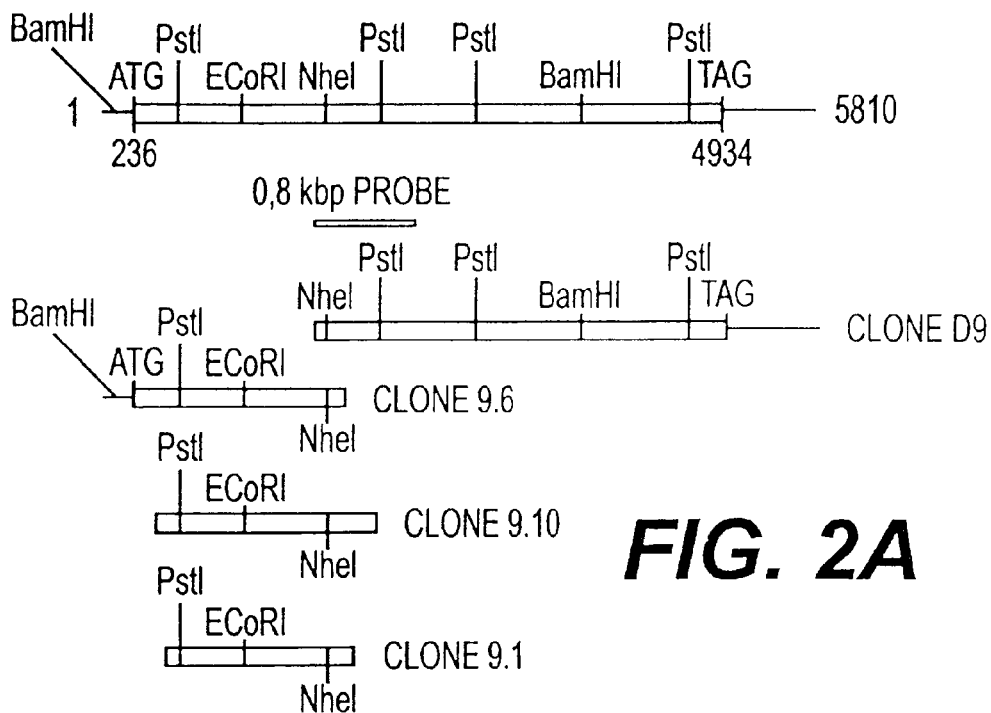

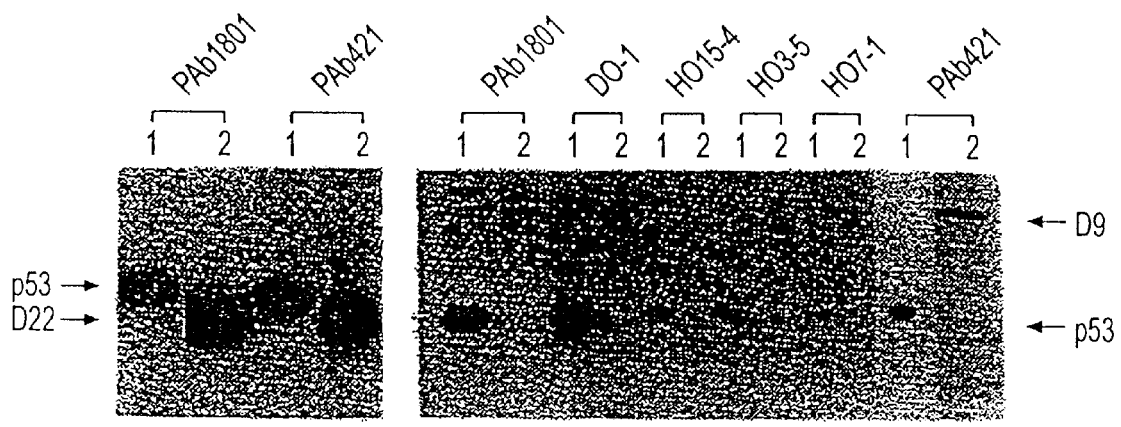
FIG. 1A1     FIG. 1A2
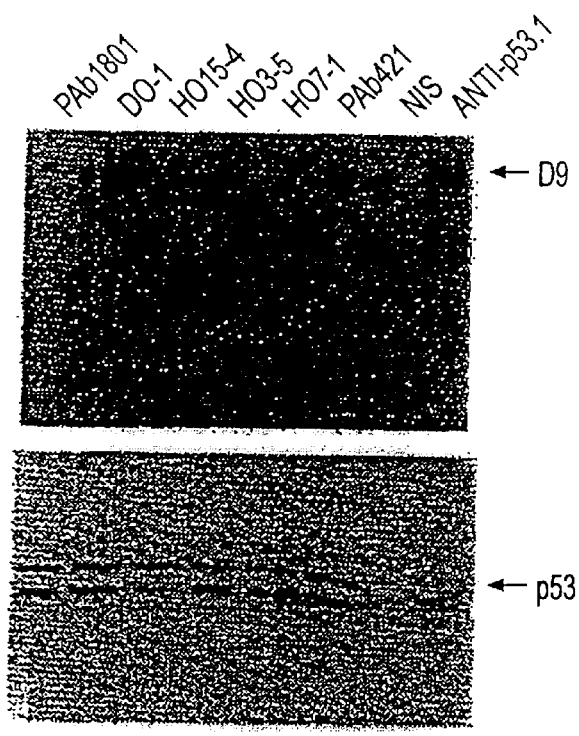
FIG. 1B1
FIG. 1B2

FIG. 3A

FIG. 3B

```
N   P   I   L   S   L   L   Q   I   T   G   N   G   S   T   I   G   S   P   T   P   P   H   H   T        613
AAC CCA ATT CTT AGT TTG TTG CAA ATC ACA GGG AAC GGG TCT ACC ATT GGC TCG AGT CCG ACC CCT CAT CAC ACG      2074

P   P   V   S   S   M   A   G   N   T   K   N   H   P   M   S   S   H   P   A   Q   D              641
CCG CCA GTC TCT TCG ATG GCC GGC AAC ACC AAG AAC CAC CCG ATG TCC ATG CCT GCC CAG GAT                      2158

F   S   T   L   Y   G   S   P   L   E   R   Q   S   N   S   M   E   I   C   N   G   S              669
TTC TCA ACC CTT TAT GGA AGC CCT TTA GAA AGG CAG AAC TCC ATG GAA ATA TGC AAT GGG AGC                      2242

N   K   T   K   K   K   S   R   L   R   H   Q   K   P   M   S   R   M   E   D   D   F   Q   R   E   L    697
AAC AAG ACC AAG AAA AAG TCA AGA TTA AGA CAC CAG AAA CCA ATG TCC CGC ATG GAA GAT GAC TTT CAG AGG GAG CTA  2326

F   S   M   D   V   C   S   T   D   S   Q   N   M   I   A   D   T   L   D   T   P   Q   H   I   T   P    725
TTT TCA ATG GAT GTT TGT TCA GAC TCA CAG AAC ATG ATA GCT GAC ACT CTG GAT ACG CCA CAA CAC ATC ACT CCA      2410

A   P   S   Q   C   S   T   P   N   P   P   Y   P   Q   V   P   P   Q   P   S   I   Q   R   M   V   R    753
GCT CCA AGC CAG TGT AGC ACT CCC AAC CCT CCA TAC CCT CAA GTA CCA CCC CAA CCC AGT ATT CAA AGG ATG GTC CGA  2494

L   S   S   D   S   I   G   I   L   D   L   S   D   I   L   A   E   E   A   S   K   L   P   S   T        781
CTA TCC AGC GAC AGC ATT GGC ATT TTA GAC CTT TCA GAT ATT GCA GAA GAA GCT TCT AAA CTT CCC AGC ACT          2578

S   D   D   C   P   A   I   R   D   P   T   P   L   R   D   S   G   H   S   Q   T   L   F   D   S   D    809
AGT GAT GAT TGC CCA GCC ATT CGA GAT CCT ACC CCT CTT CGA GAT TCA GGG CAT TCT CAG ACC CTG TTT GAC TCT GAT  2662

V   F   Q   T   N   N   N   E   N   P   Y   T   D   P   A   D   L   I   A   D   A   G   S   P   S   D    837
GTC TTT CAA ACT AAC AAT AAT GAA AAT CCT TAC ACT GAT CCT GCT GAT CTT ATT GCA GAT GCT GGA AGC CCC AGT GAT  2746

S   P   T   N   H   F   F   H   D   G   V   D   F   N   P   D   L   L   N   S   Q   S   F   G   E       865
TCT CCT ACC AAT CAT TTT TTT CAT GAT GGA GTA GAT TTC AAT CCT GAT TTA TTG AAC AGC CAG AGC TTT GGT GGA GAA  2830

E   Y   F   D   E   S   Q   N   H   F   F   D   E   K   G   F   A   S   Q   A   L   N   T   L   G   V    893
GAA TAT TTT GAT GAA AGC CAA AAT CAT TTT TTC GAT GAA AAA GGA TTT GCA TCT CAG GCA CTA AAT ACT TTG GGG GTG  2914
```

```
                                        S  H  S  I  K  P  E  S  W  S  K  S  P  I  S  D  Q  S  L  S  M  T  S  N  T  I  L   1537
                                        TCT CAT AGC ATC AAG CCA GAG AGT TGG TCC AAA TCA CCC ATC TCT TCA GAC CAG TCC TTG TCT ATG ACA AGT AAC ACA ATC TTA  4846

S  A  D  R  P  S  R  L  S  P  D  F  M  I  G  E  D  D  L  M  D  V  A  L  I  G   1565
                                        TCT GCA GAC AGA CCC TCA AGG CTC AGC CCA GAC TTT ATG ATT GGG GAG GAT GAT CTT ATG GAT GTG GCC CTG ATT GGG  4930

N                                                                                                              1566
                                        AAT taggaacctta ttcctaaagaa acagggccag aggaaaaaaa actattgata agttatatag gcaaaccacc ataagggtga gtcagacagg tctgatttgg tta   5040
                                            agaatcctaa atgcatgctt gacatcaagc tggtgtgaat tccagacata caagaaaagc atatcaaaga aaccacaggg tttgattctg ttaccaggaa gtcttctt      5152
                                            gttcctgtgc cagaaagaaa gttaaaatac ttgcttaagt gtggagggg tgaggggtg gtggaaggg aggagggaa cagtttgtgg aaatattcat atat               5264
                                            atttttctcc cttttcattt taggccatgt cagttagtc tcatttgag gtcaaattg cagggcaaat gaaaaaggt caatacatt cttgatgcat ttgc                5376
                                            atgaaggttg ttcaactttg tttgaggtag tagtccgtt tgagtcatgt ggcaaatgaa gactttggtc atttgacac tgttgtcttg tcttcttagg ag                 5488
                                            tgactgggga gggaagattat ttagctat tattgtaat atttaaccct ttatctgtt tgtttttata cagttcgtt ctaaatctat gaggttaggg ttcaaaa                5600
                                            tgatggaagg ccgaagagca aggcttatat cgtggtaggg agcttatag cttgtgcta atactgtgc tcaagccaag caaattagtc agagcccgc ctttagagtt aaa         5712
                                            tataataga aatgatattt tatttaggg gtttaaataggg ttcagagat catagatca gatcataga aatatttagg agttaccctc gtgtgggagg tat
```

*FIG. 3F*

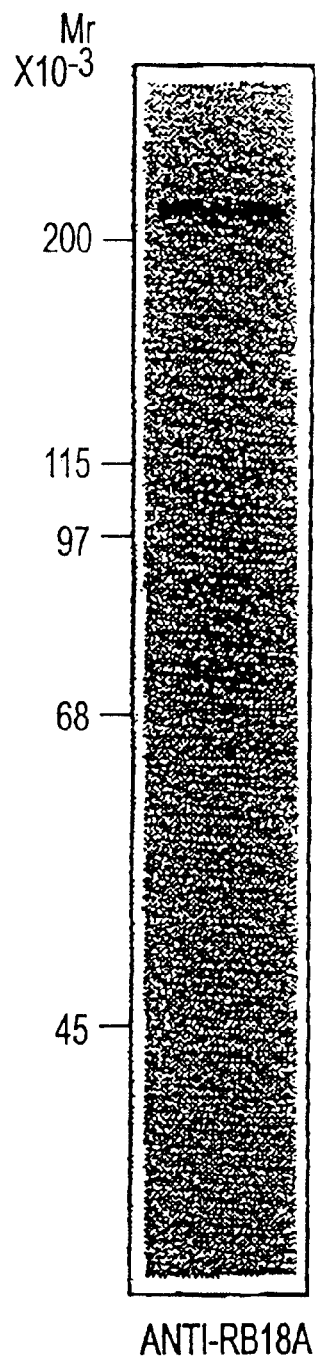
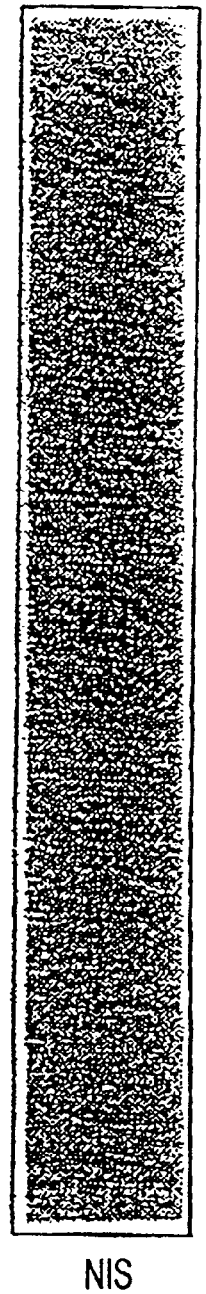
ANTI-RB18A
NIS
FIG. 4.1
FIG. 4.2

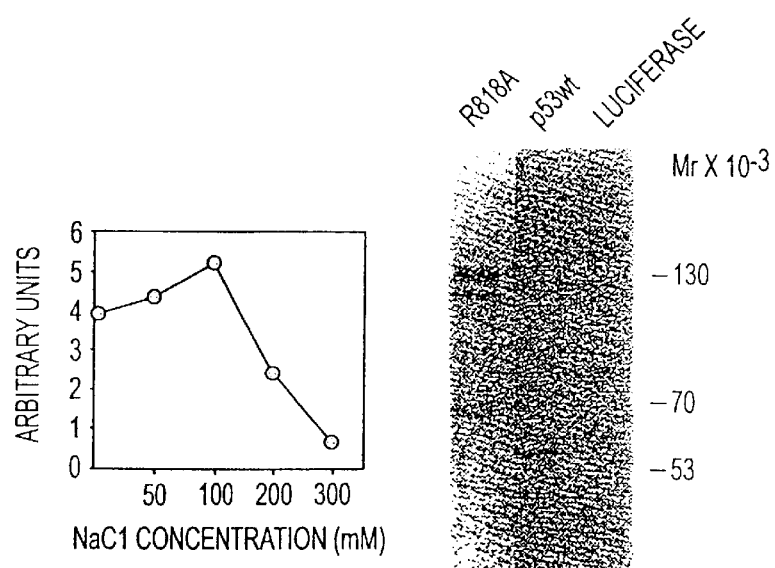
FIG. 5A
FIG. 5B
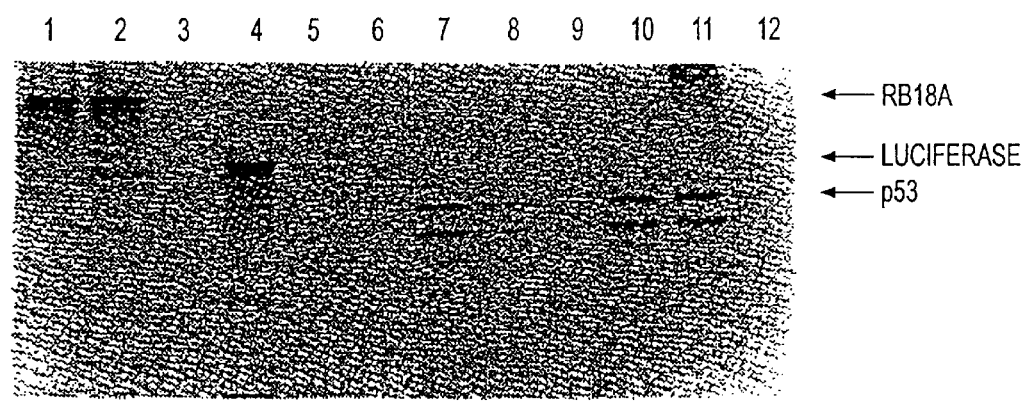
FIG. 6

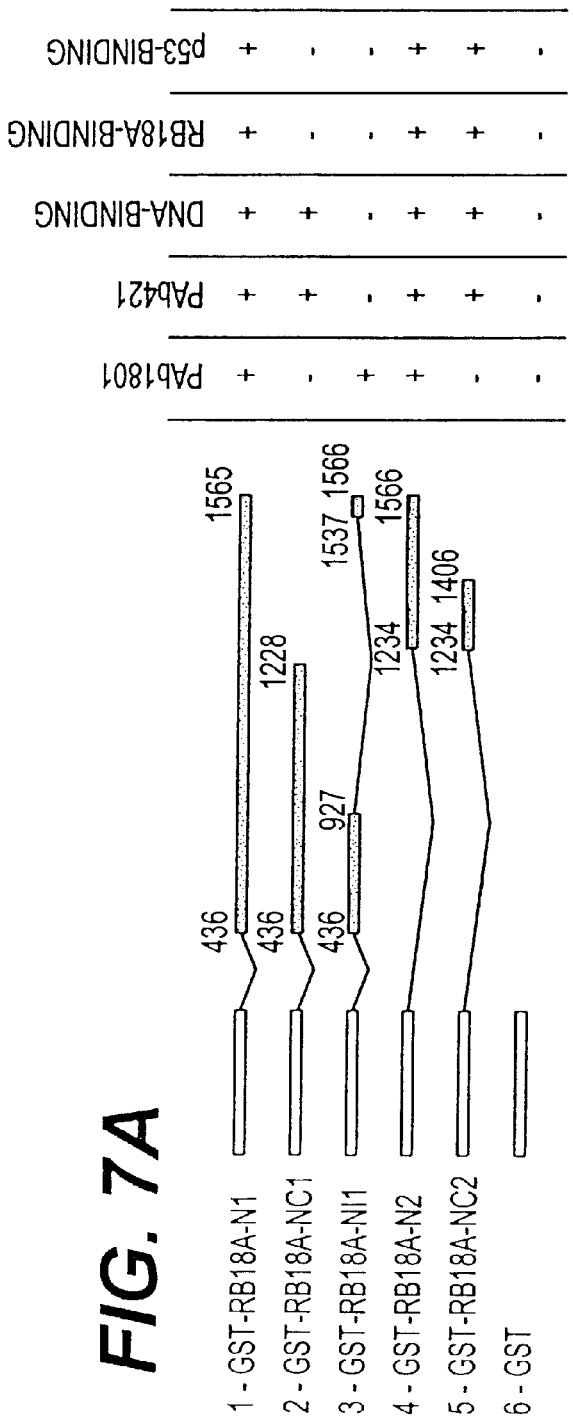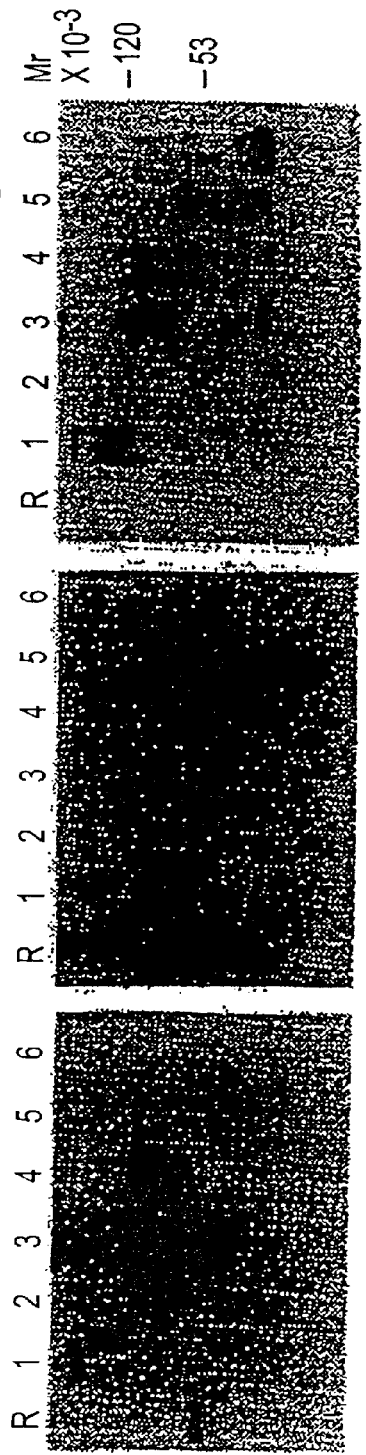

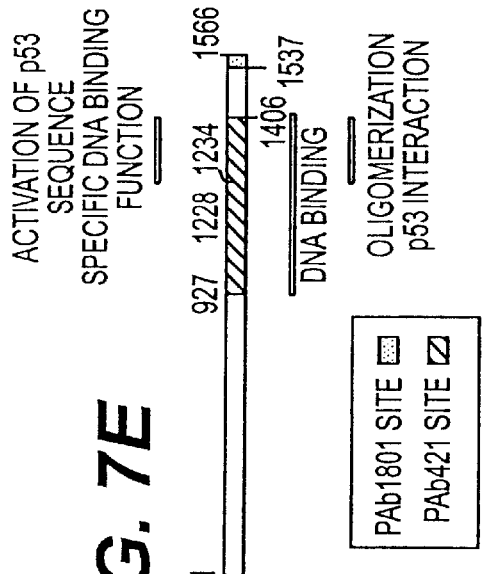
FIG. 7D
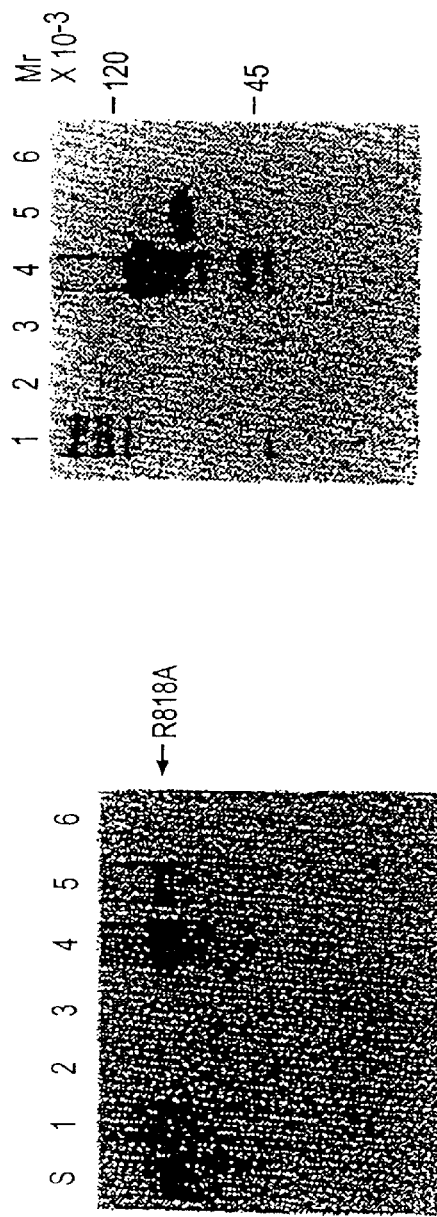
FIG. 7C1
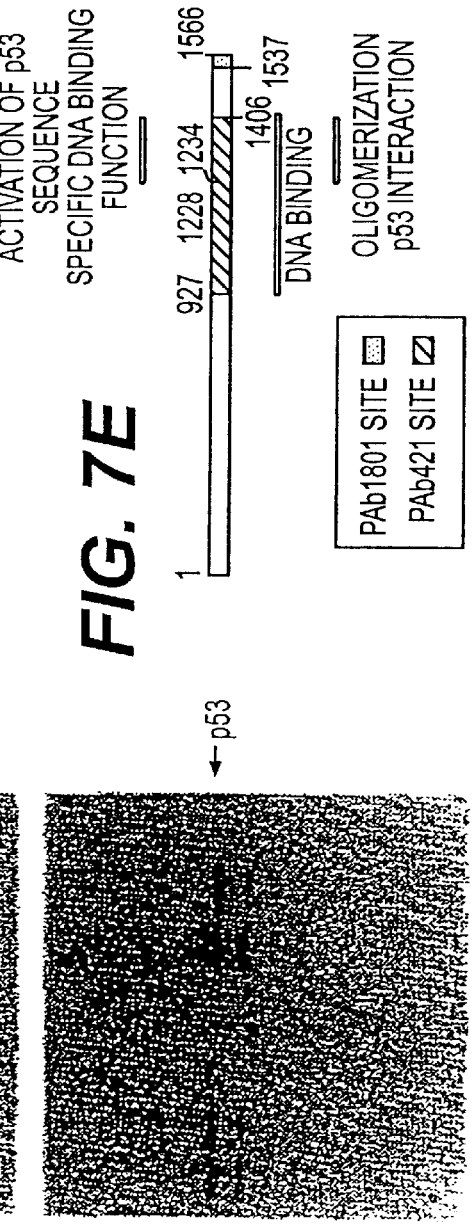
FIG. 7C2
FIG. 7E

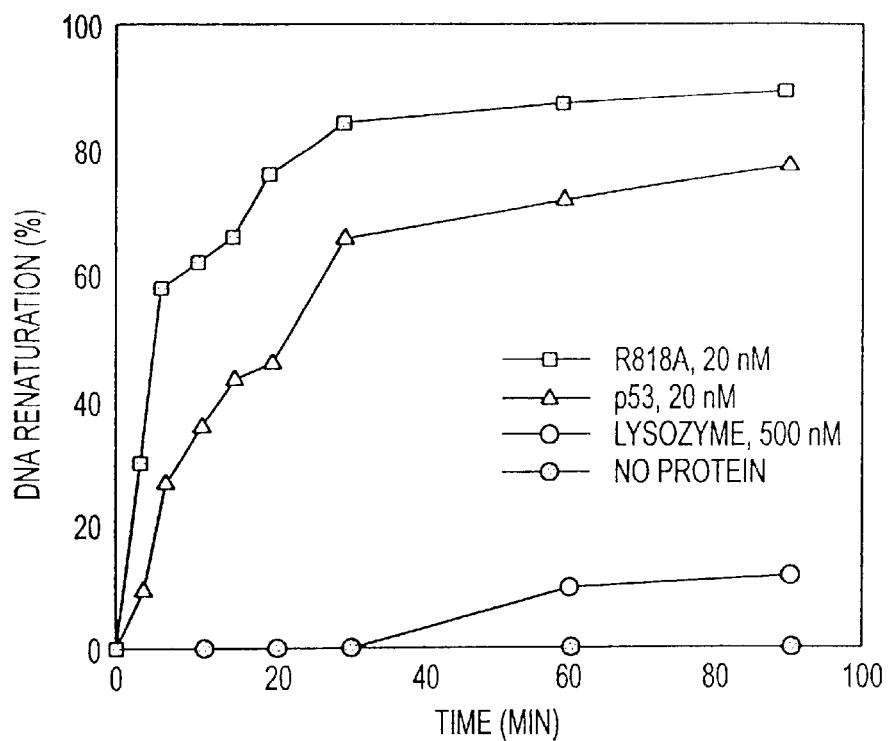
FIG. 11
FIG. 12A
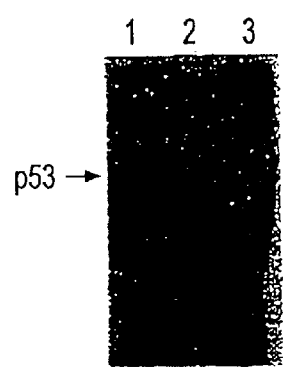
FIG. 12B
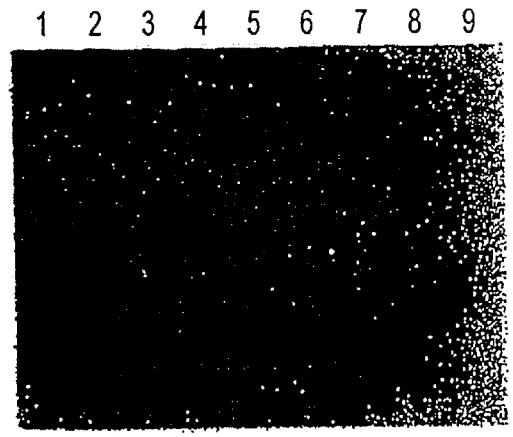

SEQUENCE LISTING

```
<160> NUMBER OF SEQ ID NOS: 10

<210> SEQ ID NO 1
<211> LENGTH: 5810
<212> TYPE: DNA
<213> ORGANISM: Homo sapiens
<220> FEATURE:
<221> NAME/KEY: CDS
<222> LOCATION: (236)..(4933)

<400> SEQUENCE: 1
gggaagatgg cggcggcctc gagcaccctc ctcttcttgc cgccggggac ttcagattga      60
tccttcccgg gaagagtagg gactgctggt gccctgcgtc ccgggatccc gagccaactt     120
gtttcctccg ttagtggtgg ggaagggctt atccttttgt ggcggatcta gcttctcctc     180
gccttcagga tgaaagctca gggggaaac cgaggagtca gaaaagctga gtaag atg       238
                                                              Met
                                                               1 agt tct ctc ctg gaa cgg ctc cat gca aaa ttt aac caa aat aga ccc       286
Ser Ser Leu Leu Glu Arg Leu His Ala Lys Phe Asn Gln Asn Arg Pro
```

```
                5                    10                   15
tgg agt gaa acc att aag ctt gtg cgt caa gtc atg gag aag agg gtt     334
Trp Ser Glu Thr Ile Lys Leu Val Arg Gln Val Met Glu Lys Arg Val
        20                  25                  30 gtg atg agt tct gga ggg cat caa cat ttg gtc agc tgt ttg gag aca     382
Val Met Ser Ser Gly Gly His Gln His Leu Val Ser Cys Leu Glu Thr
    35                  40                  45 ttg cag aag gct ctc aaa gta aca tct tta cca gca atg act gat cgt     430
Leu Gln Lys Ala Leu Lys Val Thr Ser Leu Pro Ala Met Thr Asp Arg
50                  55                  60                  65 ttg gag tcc ata gca gga cag aat gga ctg ggc tct cat ctc agt gcc     478
Leu Glu Ser Ile Ala Gly Gln Asn Gly Leu Gly Ser His Leu Ser Ala
                70                  75                  80 agt ggc act gaa tgt tac atc acg tca gat atg ttc tat gtg gaa gtg     526
Ser Gly Thr Glu Cys Tyr Ile Thr Ser Asp Met Phe Tyr Val Glu Val
            85                  90                  95 cag tta gat cct gca gga cag ctt tgt gat gta aaa gtg gct cac cat     574
Gln Leu Asp Pro Ala Gly Gln Leu Cys Asp Val Lys Val Ala His His
        100                 105                 110 ggg gag aat cct gtg agc tgt ccg gag ctt gta cag cag cta agg gaa     622
Gly Glu Asn Pro Val Ser Cys Pro Glu Leu Val Gln Gln Leu Arg Glu
    115                 120                 125 aaa aat tct gat gaa ttt tct aag cac ctt aag ggc ctt gtt aat ctg     670
Lys Asn Ser Asp Glu Phe Ser Lys His Leu Lys Gly Leu Val Asn Leu
130                 135                 140                 145 tat aac ctt cca ggg gac aac aaa ctg aag act aaa atg tac ttg gct     718
Tyr Asn Leu Pro Gly Asp Asn Lys Leu Lys Thr Lys Met Tyr Leu Ala
                150                 155                 160 ctc caa tcc tta gaa caa gat ctt tct aaa atg gca att atg tac tgg     766
Leu Gln Ser Leu Glu Gln Asp Leu Ser Lys Met Ala Ile Met Tyr Trp
            165                 170                 175 aaa gca act aat gct ggt ccc ttg gat aag att ctt cat gga agt gtt     814
Lys Ala Thr Asn Ala Gly Pro Leu Asp Lys Ile Leu His Gly Ser Val
        180                 185                 190 ggc tat ctc aca cca agg agt ggg ggt cat tta atg aac ctg aag tac     862
Gly Tyr Leu Thr Pro Arg Ser Gly Gly His Leu Met Asn Leu Lys Tyr
    195                 200                 205 tat gtc tct cct tct gac cta ctg gat gac aag act gca tct ccc atc     910
Tyr Val Ser Pro Ser Asp Leu Leu Asp Asp Lys Thr Ala Ser Pro Ile
210                 215                 220                 225 att ttg cat gag aat aat gtt tct cga tct ttg ggc atg aat gca tca     958
Ile Leu His Glu Asn Asn Val Ser Arg Ser Leu Gly Met Asn Ala Ser
                230                 235                 240 gtg aca att gaa gga aca tct gct gtg tac aaa ctc cca att gca cca    1006
Val Thr Ile Glu Gly Thr Ser Ala Val Tyr Lys Leu Pro Ile Ala Pro
            245                 250                 255 tta att atg ggg tca cat cca gtt gac aat aaa tgg acc cct tcc ttc    1054
Leu Ile Met Gly Ser His Pro Val Asp Asn Lys Trp Thr Pro Ser Phe
        260                 265                 270 tcc tca atc acc agt gcc aac agt gtt gat ctt cct gcc tgt ttc ttc    1102
Ser Ser Ile Thr Ser Ala Asn Ser Val Asp Leu Pro Ala Cys Phe Phe
    275                 280                 285 ttg aaa ttt ccc cag cca atc cca gta tct aga gca ttt gtt cag aaa    1150
Leu Lys Phe Pro Gln Pro Ile Pro Val Ser Arg Ala Phe Val Gln Lys
290                 295                 300                 305 ctg cag aac tgc aca gga att cca ttg ttt gaa act caa cca act tat    1198
Leu Gln Asn Cys Thr Gly Ile Pro Leu Phe Glu Thr Gln Pro Thr Tyr
                310                 315                 320 gca ccc ctg tat gaa ctg atc act cag ttt gag cta tca aag gac cct    1246
```

```
             Ala Pro Leu Tyr Glu Leu Ile Thr Gln Phe Glu Leu Ser Lys Asp Pro
                         325                 330                 335 gac ccc ata cct ttg aat cac aac atg aga ttt tat gct gct ctt cct        1294
Asp Pro Ile Pro Leu Asn His Asn Met Arg Phe Tyr Ala Ala Leu Pro
            340                 345                 350 ggt cag cag cac tgc tat ttc ctc aac aag gat gct cct ctt cca gat        1342
Gly Gln Gln His Cys Tyr Phe Leu Asn Lys Asp Ala Pro Leu Pro Asp
        355                 360                 365 ggc cga agt cta cag gga acc ctt gtt agc aaa atc acc ttt cag cac        1390
Gly Arg Ser Leu Gln Gly Thr Leu Val Ser Lys Ile Thr Phe Gln His
370                 375                 380                 385 cct ggc cga gtt cct ctt atc cta aat ctg atc aga cac caa gtg gcc        1438
Pro Gly Arg Val Pro Leu Ile Leu Asn Leu Ile Arg His Gln Val Ala
                390                 395                 400 tat aac acc ctc att gga agc tgt gtc aaa aga act att ctg aaa gaa        1486
Tyr Asn Thr Leu Ile Gly Ser Cys Val Lys Arg Thr Ile Leu Lys Glu
            405                 410                 415 gat tct cct ggg ctt ctc caa ttt gaa gtg tgt cct ctc tca gag tct        1534
Asp Ser Pro Gly Leu Leu Gln Phe Glu Val Cys Pro Leu Ser Glu Ser
        420                 425                 430 cgt ttc agc gta tct ttt cag cac cct gtg aat gac tcc ctg gtg tgt        1582
Arg Phe Ser Val Ser Phe Gln His Pro Val Asn Asp Ser Leu Val Cys
435                 440                 445 gtg gta atg gat gtg cag ggc tta aca cat gtg agc tgt aaa ctc tac        1630
Val Val Met Asp Val Gln Gly Leu Thr His Val Ser Cys Lys Leu Tyr
450                 455                 460                 465 aaa ggg ctg tcg gat gca ctg atc tgc aca gat gac ttc att gcc aaa        1678
Lys Gly Leu Ser Asp Ala Leu Ile Cys Thr Asp Asp Phe Ile Ala Lys
                470                 475                 480 gtt gtt caa aga tgt atg tcc atc cct gtg acg atg agg gct att cgg        1726
Val Val Gln Arg Cys Met Ser Ile Pro Val Thr Met Arg Ala Ile Arg
            485                 490                 495 agg aaa gct gaa acc att caa gcc gac acc cca gca ctg tcc ctc att        1774
Arg Lys Ala Glu Thr Ile Gln Ala Asp Thr Pro Ala Leu Ser Leu Ile
        500                 505                 510 gca gag aca gtt gaa gac atg gtg aaa aag aac ctg ccc ccg gct agc        1822
Ala Glu Thr Val Glu Asp Met Val Lys Lys Asn Leu Pro Pro Ala Ser
515                 520                 525 agc cca ggg tat ggc atg acc aca ggc aac aac cca atg agt ggt acc        1870
Ser Pro Gly Tyr Gly Met Thr Thr Gly Asn Asn Pro Met Ser Gly Thr
530                 535                 540                 545 act aca tca acc aac acc ttt ccg ggg ggt ccc att gcc acc ttg ttt        1918
Thr Thr Ser Thr Asn Thr Phe Pro Gly Gly Pro Ile Ala Thr Leu Phe
                550                 555                 560 aat atg agc atg agc atc aaa gat cgg cat gag tcg gtg ggc cat ggg        1966
Asn Met Ser Met Ser Ile Lys Asp Arg His Glu Ser Val Gly His Gly
            565                 570                 575 gag gac ttc agc aag gtg tct cag aac cca att ctt acc agt ttg ttg        2014
Glu Asp Phe Ser Lys Val Ser Gln Asn Pro Ile Leu Thr Ser Leu Leu
        580                 585                 590 caa atc aca ggg aac ggg ggg tct acc att ggc tcg agt ccg acc cct        2062
Gln Ile Thr Gly Asn Gly Gly Ser Thr Ile Gly Ser Ser Pro Thr Pro
595                 600                 605 cct cat cac acg ccg cca cct gtc tct tcg atg gcc ggc aac acc aag        2110
Pro His His Thr Pro Pro Pro Val Ser Ser Met Ala Gly Asn Thr Lys
610                 615                 620                 625 aac cac ccg atg ctc atg aac ctt ctc aaa gat aat cct gcc cag gat        2158
Asn His Pro Met Leu Met Asn Leu Leu Lys Asp Asn Pro Ala Gln Asp
                630                 635                 640
```

-continued

| | |
|---|---|
| ttc tca acc ctt tat gga agc agc cct tta gaa agg cag aac tcc tct<br>Phe Ser Thr Leu Tyr Gly Ser Ser Pro Leu Glu Arg Gln Asn Ser Ser<br>               645                   650                   655 | 2206 |
| tcc ggc tca ccc cgc atg gaa ata tgc tcg ggg agc aac aag acc aag<br>Ser Gly Ser Pro Arg Met Glu Ile Cys Ser Gly Ser Asn Lys Thr Lys<br>        660                   665                   670 | 2254 |
| aaa aag aag tca tca aga tta cca cct gag aaa cca aag cac cag act<br>Lys Lys Lys Ser Ser Arg Leu Pro Pro Glu Lys Pro Lys His Gln Thr<br>675                   680                   685 | 2302 |
| gaa gat gac ttt cag agg gag cta ttt tca atg gat gtt gac tca cag<br>Glu Asp Asp Phe Gln Arg Glu Leu Phe Ser Met Asp Val Asp Ser Gln<br>690                   695                   700                   705 | 2350 |
| aac cct atc ttt gat gtc aac atg aca gct gac acg ctg gat acg cca<br>Asn Pro Ile Phe Asp Val Asn Met Thr Ala Asp Thr Leu Asp Thr Pro<br>               710                   715                   720 | 2398 |
| cac atc act cca gct cca agc cag tgt agc act ccc cca aca act tac<br>His Ile Thr Pro Ala Pro Ser Gln Cys Ser Thr Pro Pro Thr Thr Tyr<br>              725                   730                   735 | 2446 |
| cca caa cca gta cct cac ccc caa ccc agt att caa agg atg gtc cga<br>Pro Gln Pro Val Pro His Pro Gln Pro Ser Ile Gln Arg Met Val Arg<br>        740                   745                   750 | 2494 |
| cta tcc agt tca gac agc att ggc cca gat gta act gac atc ctt tca<br>Leu Ser Ser Ser Asp Ser Ile Gly Pro Asp Val Thr Asp Ile Leu Ser<br>755                   760                   765 | 2542 |
| gac att gca gaa gaa gct tct aaa ctt ccc agc act agt gat gat tgc<br>Asp Ile Ala Glu Glu Ala Ser Lys Leu Pro Ser Thr Ser Asp Asp Cys<br>770                   775                   780                   785 | 2590 |
| cca gcc att ggc acc cct ctt cga gat tct tca agc tct ggg cat tct<br>Pro Ala Ile Gly Thr Pro Leu Arg Asp Ser Ser Ser Ser Gly His Ser<br>               790                   795                   800 | 2638 |
| cag agt acc ctg ttt gac tct gat gtc ttt caa act aac aat aat gaa<br>Gln Ser Thr Leu Phe Asp Ser Asp Val Phe Gln Thr Asn Asn Asn Glu<br>805                   810                   815 | 2686 |
| aat cca tac act gat cca gct gat ctt att gca gat gct gct gga agc<br>Asn Pro Tyr Thr Asp Pro Ala Asp Leu Ile Ala Asp Ala Ala Gly Ser<br>820                   825                   830 | 2734 |
| ccc agt agt gac tct cct acc aat cat ttt ttt cat gat gga gta gat<br>Pro Ser Ser Asp Ser Pro Thr Asn His Phe Phe His Asp Gly Val Asp<br>835                   840                   845 | 2782 |
| ttc aat cct gat tta ttg aac agc cag agc caa agt ggt ttt gga gaa<br>Phe Asn Pro Asp Leu Leu Asn Ser Gln Ser Gln Ser Gly Phe Gly Glu<br>850                   855                   860                   865 | 2830 |
| gaa tat ttt gat gaa agc agc caa agt ggg gat aat gat gat ttc aaa<br>Glu Tyr Phe Asp Glu Ser Ser Gln Ser Gly Asp Asn Asp Asp Phe Lys<br>               870                   875                   880 | 2878 |
| gga ttt gca tct cag gca cta aat act ttg ggg gtg cca atg ctt gga<br>Gly Phe Ala Ser Gln Ala Leu Asn Thr Leu Gly Val Pro Met Leu Gly<br>        885                   890                   895 | 2926 |
| ggt gat aat ggg gag acc aag ttt aag ggc aat aac caa gcc gac aca<br>Gly Asp Asn Gly Glu Thr Lys Phe Lys Gly Asn Asn Gln Ala Asp Thr<br>               900                   905                   910 | 2974 |
| gtt gat ttc agt att att tca gta gcc ggc aaa gct tta gct cct gca<br>Val Asp Phe Ser Ile Ile Ser Val Ala Gly Lys Ala Leu Ala Pro Ala<br>915                   920                   925 | 3022 |
| gat ctt atg gag cat cac agt ggt agt cag ggt cct tta ctg acc act<br>Asp Leu Met Glu His His Ser Gly Ser Gln Gly Pro Leu Leu Thr Thr<br>930                   935                   940                   945 | 3070 |
| ggg gac tta ggg aaa gaa aag act caa aag agg gta aag gaa ggc aat<br>Gly Asp Leu Gly Lys Glu Lys Thr Gln Lys Arg Val Lys Glu Gly Asn<br>               950                   955                   960 | 3118 |

| | | |
|---|---|---|
| ggc acc agt aat agt act ctc tcg ggg ccc gga tta gac agc aaa cca<br>Gly Thr Ser Asn Ser Thr Leu Ser Gly Pro Gly Leu Asp Ser Lys Pro<br>          965                    970                    975 | 3166 |
| ggg aag cgc agt cgg acc cct tct aat gat ggg aaa agc aaa gat aag<br>Gly Lys Arg Ser Arg Thr Pro Ser Asn Asp Gly Lys Ser Lys Asp Lys<br>          980                    985                    990 | 3214 |
| cct cca aag cgg aag aag gca gac act gag gga aag tct cca tct cat<br>Pro Pro Lys Arg Lys Lys Ala Asp Thr Glu Gly Lys Ser Pro Ser His<br>          995                    1000               1005 | 3262 |
| agt tct tct aac aga cct ttt acc cca cct acc agt aca ggt gga<br>Ser Ser Ser Asn Arg Pro Phe Thr Pro Pro Thr Ser Thr Gly Gly<br>1010                    1015                    1020 | 3307 |
| tct aaa tcg cca ggc agt gca gga aga tct cag act ccc cca ggt<br>Ser Lys Ser Pro Gly Ser Ala Gly Arg Ser Gln Thr Pro Pro Gly<br>1025                    1030                    1035 | 3352 |
| gtt gcc aca cca ccc att ccc aaa atc act att cag att cct aag<br>Val Ala Thr Pro Pro Ile Pro Lys Ile Thr Ile Gln Ile Pro Lys<br>1040                    1045                    1050 | 3397 |
| gga aca gtg atg gtg ggc aag cct tcc tct cac agt cag tat acc<br>Gly Thr Val Met Val Gly Lys Pro Ser Ser His Ser Gln Tyr Thr<br>1055                    1060                    1065 | 3442 |
| agc agt ggt tct gtg tct tcc tca ggc agc aaa agc cac cat agc<br>Ser Ser Gly Ser Val Ser Ser Ser Gly Ser Lys Ser His His Ser<br>1070                    1075                    1080 | 3487 |
| cat tct tcc tcc tct tcc tca tct gct tcc acc tca ggg aag atg<br>His Ser Ser Ser Ser Ser Ser Ser Ala Ser Thr Ser Gly Lys Met<br>1085                    1090                    1095 | 3532 |
| aaa agc agt aaa tca gaa ggt tca tca agt tcc aag tta agt agc<br>Lys Ser Ser Lys Ser Glu Gly Ser Ser Ser Lys Leu Ser Ser<br>1100                    1105                    1110 | 3577 |
| agt atg tat tct agc cag ggg tct tct gga tct agc cag tcc aaa<br>Ser Met Tyr Ser Ser Gln Gly Ser Ser Gly Ser Ser Gln Ser Lys<br>1115                    1120                    1125 | 3622 |
| aat tca tcc cag tct ggg ggg aag cca ggc tct tct ccc ata acc<br>Asn Ser Ser Gln Ser Gly Gly Lys Pro Gly Ser Ser Pro Ile Thr<br>1130                    1135                    1140 | 3667 |
| aag cat gga ctg agc agt ggc tct agc agc acc aag atg aaa cct<br>Lys His Gly Leu Ser Ser Gly Ser Ser Ser Thr Lys Met Lys Pro<br>1145                    1150                    1155 | 3712 |
| caa gga aag cca tca tca ctt atg aat cct tct tta agt aaa cca<br>Gln Gly Lys Pro Ser Ser Leu Met Asn Pro Ser Leu Ser Lys Pro<br>1160                    1165                    1170 | 3757 |
| aac ata tcc cct tct cat tca agg cca cct gga ggc tct gac aag<br>Asn Ile Ser Pro Ser His Ser Arg Pro Pro Gly Gly Ser Asp Lys<br>1175                    1180                    1185 | 3802 |
| ctt gcc tct cca atg aag cct gtt cct gga act cct cca tcc tct<br>Leu Ala Ser Pro Met Lys Pro Val Pro Gly Thr Pro Pro Ser Ser<br>1190                    1195                    1200 | 3847 |
| aaa gcc aag tcc cct atc agt tca ggt tct ggt ggt tct cat atg<br>Lys Ala Lys Ser Pro Ile Ser Ser Gly Ser Gly Gly Ser His Met<br>1205                    1210                    1215 | 3892 |
| tct gga act agt tca agc tct ggc atg aag tca tct tca ggg tta<br>Ser Gly Thr Ser Ser Ser Ser Gly Met Lys Ser Ser Ser Gly Leu<br>1220                    1225                    1230 | 3937 |
| gga tcc tca ggc tcg ttg tcc cag aaa act ccc cca tca tct aat<br>Gly Ser Ser Gly Ser Leu Ser Gln Lys Thr Pro Pro Ser Ser Asn<br>1235                    1240                    1245 | 3982 |
| tcc tgt acg gca tct tcc tcc tcc ttt tcc tca agt ggc tct tcc<br>Ser Cys Thr Ala Ser Ser Ser Ser Phe Ser Ser Ser Gly Ser Ser | 4027 |

-continued

| | | | | | | | | | | | | | | |
|---|---|---|---|---|---|---|---|---|---|---|---|---|---|---|
| | 1250 | | | | 1255 | | | | | 1260 | | | | |
| atg | tca | tcc | tct | cag | aac | cag | cat | ggg | agt | tct | aaa | gga | aaa | tct | 4072 |
| Met | Ser | Ser | Ser | Gln | Asn | Gln | His | Gly | Ser | Ser | Lys | Gly | Lys | Ser | |
| 1265 | | | | | 1270 | | | | | 1275 | | | | | |
| ccc | agc | aga | aac | aag | aag | ccg | tcc | ttg | aca | gct | gtc | ata | gat | aaa | 4117 |
| Pro | Ser | Arg | Asn | Lys | Lys | Pro | Ser | Leu | Thr | Ala | Val | Ile | Asp | Lys | |
| 1280 | | | | | 1285 | | | | | 1290 | | | | | |
| ctg | aag | cat | ggg | gtt | gtc | acc | agt | ggc | cct | ggg | ggt | gaa | gac | cca | 4162 |
| Leu | Lys | His | Gly | Val | Val | Thr | Ser | Gly | Pro | Gly | Gly | Glu | Asp | Pro | |
| 1295 | | | | | 1300 | | | | | 1305 | | | | | |
| ctg | gac | ggc | cag | atg | ggg | gtg | agc | aca | aat | tct | tcc | agc | cat | cct | 4207 |
| Leu | Asp | Gly | Gln | Met | Gly | Val | Ser | Thr | Asn | Ser | Ser | Ser | His | Pro | |
| 1310 | | | | | 1315 | | | | | 1320 | | | | | |
| atg | tcc | tcc | aaa | cat | aac | atg | tca | gga | gga | gag | ttt | cag | ggc | aag | 4252 |
| Met | Ser | Ser | Lys | His | Asn | Met | Ser | Gly | Gly | Glu | Phe | Gln | Gly | Lys | |
| 1325 | | | | | 1330 | | | | | 1335 | | | | | |
| cgt | gag | aaa | agt | gat | aaa | gac | aaa | tca | aag | gtt | tcc | acc | tcc | ggg | 4297 |
| Arg | Glu | Lys | Ser | Asp | Lys | Asp | Lys | Ser | Lys | Val | Ser | Thr | Ser | Gly | |
| 1340 | | | | | 1345 | | | | | 1350 | | | | | |
| agt | tca | gtg | gat | tct | tct | aag | aag | acc | tca | gag | tca | aaa | aat | gtg | 4342 |
| Ser | Ser | Val | Asp | Ser | Ser | Lys | Lys | Thr | Ser | Glu | Ser | Lys | Asn | Val | |
| 1355 | | | | | 1360 | | | | | 1365 | | | | | |
| ggg | agc | aca | ggt | gtg | gca | aaa | att | atc | atc | agt | aag | cat | gat | gga | 4387 |
| Gly | Ser | Thr | Gly | Val | Ala | Lys | Ile | Ile | Ile | Ser | Lys | His | Asp | Gly | |
| 1370 | | | | | 1375 | | | | | 1380 | | | | | |
| ggc | tcc | cct | agc | att | aaa | gcc | aaa | gtg | act | ttg | cag | aaa | cct | ggg | 4432 |
| Gly | Ser | Pro | Ser | Ile | Lys | Ala | Lys | Val | Thr | Leu | Gln | Lys | Pro | Gly | |
| 1385 | | | | | 1390 | | | | | 1395 | | | | | |
| gaa | agt | agt | gga | gaa | ggg | ctt | agg | cct | caa | atg | gct | tct | tct | aaa | 4477 |
| Glu | Ser | Ser | Gly | Glu | Gly | Leu | Arg | Pro | Gln | Met | Ala | Ser | Ser | Lys | |
| 1400 | | | | | 1405 | | | | | 1410 | | | | | |
| aac | tat | ggc | tct | cca | ctc | atc | agt | ggt | tcc | act | cca | aag | cat | gag | 4522 |
| Asn | Tyr | Gly | Ser | Pro | Leu | Ile | Ser | Gly | Ser | Thr | Pro | Lys | His | Glu | |
| 1415 | | | | | 1420 | | | | | 1425 | | | | | |
| cgt | ggc | tct | ccc | agc | cat | agt | aag | tca | cca | gca | tat | acc | ccc | cag | 4567 |
| Arg | Gly | Ser | Pro | Ser | His | Ser | Lys | Ser | Pro | Ala | Tyr | Thr | Pro | Gln | |
| 1430 | | | | | 1435 | | | | | 1440 | | | | | |
| aat | ctg | gac | agt | gaa | agt | gag | tca | ggc | tcc | tcc | ata | gca | gag | aaa | 4612 |
| Asn | Leu | Asp | Ser | Glu | Ser | Glu | Ser | Gly | Ser | Ser | Ile | Ala | Glu | Lys | |
| 1445 | | | | | 1450 | | | | | 1455 | | | | | |
| tct | tat | cag | aat | agt | ccc | agc | tca | gac | gat | ggt | atc | cga | cca | ctt | 4657 |
| Ser | Tyr | Gln | Asn | Ser | Pro | Ser | Ser | Asp | Asp | Gly | Ile | Arg | Pro | Leu | |
| 1460 | | | | | 1465 | | | | | 1470 | | | | | |
| cca | gaa | tac | agc | aca | gag | aaa | cat | aag | aag | cac | aaa | aag | gaa | aag | 4702 |
| Pro | Glu | Tyr | Ser | Thr | Glu | Lys | His | Lys | Lys | His | Lys | Lys | Glu | Lys | |
| 1475 | | | | | 1480 | | | | | 1485 | | | | | |
| aag | aaa | gta | aaa | gac | aaa | gat | agg | gac | cga | gac | cgg | gac | aaa | gac | 4747 |
| Lys | Lys | Val | Lys | Asp | Lys | Asp | Arg | Asp | Arg | Asp | Arg | Asp | Lys | Asp | |
| 1490 | | | | | 1495 | | | | | 1500 | | | | | |
| cga | gac | aag | aaa | aaa | tct | cat | agc | atc | aag | cca | gag | agt | tgg | tcc | 4792 |
| Arg | Asp | Lys | Lys | Lys | Ser | His | Ser | Ile | Lys | Pro | Glu | Ser | Trp | Ser | |
| 1505 | | | | | 1510 | | | | | 1515 | | | | | |
| aaa | tca | ccc | atc | tct | tca | gac | cag | tcc | ttg | tct | atg | aca | agt | aac | 4837 |
| Lys | Ser | Pro | Ile | Ser | Ser | Asp | Gln | Ser | Leu | Ser | Met | Thr | Ser | Asn | |
| 1520 | | | | | 1525 | | | | | 1530 | | | | | |
| aca | atc | tta | tct | gca | gac | aga | ccc | tca | agg | ctc | agc | cca | gac | ttt | 4882 |
| Thr | Ile | Leu | Ser | Ala | Asp | Arg | Pro | Ser | Arg | Leu | Ser | Pro | Asp | Phe | |
| 1535 | | | | | 1540 | | | | | 1545 | | | | | |
| atg | att | ggg | gag | gaa | gat | gat | gat | ctt | atg | gat | gtg | gcc | ctg | att | 4927 |

```
Met Ile Gly Glu Glu Asp Asp Asp Leu Met Asp Val Ala Leu Ile
1550                1555                1560 ggg aat taggaacctt atttcctaaa agaaacaggg ccagaggaaa aaaaactatt      4983
Gly Asn
1565 gataagttta taggcaaacc accataaggg gtgagtcaga caggtctgat ttggttaaga   5043
atcctaaatg gcatggcttt gacatcaagc tgggtgaatt agaaaggcat atccagaccc   5103
tattaaagaa accacagggt tgattctggg ttaccaggaa gtcttctttg ttcctgtgcc   5163
agaaagaaag ttaaaatact tgcttaagaa agggaggggg gtgggagggg tgtagggaga   5223
gggaagggag ggaaacagtt ttgtgggaaa tattcatata tattttcttc tcccttttttc  5283
cattttaggg ccatgtttta aactcatttt agtgcatgta tatgaaggc tgggcagaaa    5343
atgaaaaagc aatacattcc ttgatgcatt tgcatgaagg ttgttcaact ttgtttgagg   5403
tagttgtccg tttgagtcat gggcaaatga aggactttgg tcattttgga cacttaagta   5463
atgtttggtg tctgtttctt aggagtgact gggggaggga agattatttt agctatttat   5523
ttgtaatatt ttaacccttt atctgtttgt ttttatacag tgtttcgttc taaatctatg   5583
aggtttaggg ttcaaaatga tggaaggccg aagagcaagg cttatatggt ggtagggagc   5643
ttatagcttg tgctaatact gtagcatcaa gcccaagcaa attagtcaga gcccgccttt   5703
agagttaaat ataatagaaa aaccaaaatg atatttttat tttaggaggg tttaaatagg   5763
gttcagagat cataggaata ttaggagtta cctctctgtg gaggtat                5810

<210> SEQ ID NO 2
<211> LENGTH: 1566
<212> TYPE: PRT
<213> ORGANISM: Homo sapiens

<400> SEQUENCE: 2

Met Ser Ser Leu Leu Glu Arg Leu His Ala Lys Phe Asn Gln Asn Arg
1               5                   10                  15

Pro Trp Ser Glu Thr Ile Lys Leu Val Arg Gln Val Met Glu Lys Arg
            20                  25                  30

Val Val Met Ser Ser Gly Gly His Gln His Leu Val Ser Cys Leu Glu
        35                  40                  45

Thr Leu Gln Lys Ala Leu Lys Val Thr Ser Leu Pro Ala Met Thr Asp
    50                  55                  60

Arg Leu Glu Ser Ile Ala Gly Gln Asn Gly Leu Gly Ser His Leu Ser
65                  70                  75                  80

Ala Ser Gly Thr Glu Cys Tyr Ile Thr Ser Asp Met Phe Tyr Val Glu
                85                  90                  95

Val Gln Leu Asp Pro Ala Gly Gln Leu Cys Asp Val Lys Val Ala His
            100                 105                 110

His Gly Glu Asn Pro Val Ser Cys Pro Glu Leu Val Gln Gln Leu Arg
        115                 120                 125

Glu Lys Asn Ser Asp Glu Phe Ser Lys His Leu Lys Gly Leu Val Asn
    130                 135                 140

Leu Tyr Asn Leu Pro Gly Asp Asn Lys Leu Lys Thr Lys Met Tyr Leu
145                 150                 155                 160

Ala Leu Gln Ser Leu Glu Gln Asp Leu Ser Lys Met Ala Ile Met Tyr
                165                 170                 175

Trp Lys Ala Thr Asn Ala Gly Pro Leu Asp Lys Ile Leu His Gly Ser
            180                 185                 190
```

```
Val Gly Tyr Leu Thr Pro Arg Ser Gly His Leu Met Asn Leu Lys
    195                 200                 205

Tyr Tyr Val Ser Pro Ser Asp Leu Leu Asp Asp Lys Thr Ala Ser Pro
210                 215                 220

Ile Ile Leu His Glu Asn Asn Val Ser Arg Ser Leu Gly Met Asn Ala
225                 230                 235                 240

Ser Val Thr Ile Glu Gly Thr Ser Ala Val Tyr Lys Leu Pro Ile Ala
                245                 250                 255

Pro Leu Ile Met Gly Ser His Pro Val Asp Asn Lys Trp Thr Pro Ser
                260                 265                 270

Phe Ser Ser Ile Thr Ser Ala Asn Ser Val Asp Leu Pro Ala Cys Phe
        275                 280                 285

Phe Leu Lys Phe Pro Gln Pro Ile Pro Val Ser Arg Ala Phe Val Gln
290                 295                 300

Lys Leu Gln Asn Cys Thr Gly Ile Pro Leu Phe Glu Thr Gln Pro Thr
305                 310                 315                 320

Tyr Ala Pro Leu Tyr Glu Leu Ile Thr Gln Phe Glu Leu Ser Lys Asp
                325                 330                 335

Pro Asp Pro Ile Pro Leu Asn His Asn Met Arg Phe Tyr Ala Ala Leu
                340                 345                 350

Pro Gly Gln Gln His Cys Tyr Phe Leu Asn Lys Asp Ala Pro Leu Pro
        355                 360                 365

Asp Gly Arg Ser Leu Gln Gly Thr Leu Val Ser Lys Ile Thr Phe Gln
370                 375                 380

His Pro Gly Arg Val Pro Leu Ile Leu Asn Leu Ile Arg His Gln Val
385                 390                 395                 400

Ala Tyr Asn Thr Leu Ile Gly Ser Cys Val Lys Arg Thr Ile Leu Lys
                405                 410                 415

Glu Asp Ser Pro Gly Leu Leu Gln Phe Glu Val Cys Pro Leu Ser Glu
                420                 425                 430

Ser Arg Phe Ser Val Ser Phe Gln His Pro Val Asn Asp Ser Leu Val
        435                 440                 445

Cys Val Val Met Asp Val Gln Gly Leu Thr His Val Ser Cys Lys Leu
    450                 455                 460

Tyr Lys Gly Leu Ser Asp Ala Leu Ile Cys Thr Asp Asp Phe Ile Ala
465                 470                 475                 480

Lys Val Val Gln Arg Cys Met Ser Ile Pro Val Thr Met Arg Ala Ile
                485                 490                 495

Arg Arg Lys Ala Glu Thr Ile Gln Ala Asp Thr Pro Ala Leu Ser Leu
                500                 505                 510

Ile Ala Glu Thr Val Glu Asp Met Val Lys Lys Asn Leu Pro Pro Ala
        515                 520                 525

Ser Ser Pro Gly Tyr Gly Met Thr Thr Gly Asn Asn Pro Met Ser Gly
530                 535                 540

Thr Thr Thr Ser Thr Asn Thr Phe Pro Gly Gly Pro Ile Ala Thr Leu
545                 550                 555                 560

Phe Asn Met Ser Met Ser Ile Lys Asp Arg His Glu Ser Val Gly His
                565                 570                 575

Gly Glu Asp Phe Ser Lys Val Ser Gln Asn Pro Ile Leu Thr Ser Leu
            580                 585                 590

Leu Gln Ile Thr Gly Asn Gly Gly Ser Thr Ile Gly Ser Ser Pro Thr
            595                 600                 605

Pro Pro His His Thr Pro Pro Val Ser Ser Met Ala Gly Asn Thr
```

-continued

```
              610                 615                 620
Lys Asn His Pro Met Leu Met Asn Leu Leu Lys Asp Asn Pro Ala Gln
625                 630                 635                 640

Asp Phe Ser Thr Leu Tyr Gly Ser Ser Pro Leu Glu Arg Gln Asn Ser
                645                 650                 655

Ser Ser Gly Ser Pro Arg Met Glu Ile Cys Ser Gly Ser Asn Lys Thr
                660                 665                 670

Lys Lys Lys Lys Ser Ser Arg Leu Pro Pro Glu Lys Pro Lys His Gln
            675                 680                 685

Thr Glu Asp Asp Phe Gln Arg Glu Leu Phe Ser Met Asp Val Asp Ser
690                 695                 700

Gln Asn Pro Ile Phe Asp Val Asn Met Thr Ala Asp Thr Leu Asp Thr
705                 710                 715                 720

Pro His Ile Thr Pro Ala Pro Ser Gln Cys Ser Thr Pro Pro Thr Thr
                725                 730                 735

Tyr Pro Gln Pro Val Pro His Pro Gln Pro Ser Ile Gln Arg Met Val
                740                 745                 750

Arg Leu Ser Ser Ser Asp Ser Ile Gly Pro Asp Val Thr Asp Ile Leu
                755                 760                 765

Ser Asp Ile Ala Glu Glu Ala Ser Lys Leu Pro Ser Thr Ser Asp Asp
770                 775                 780

Cys Pro Ala Ile Gly Thr Pro Leu Arg Asp Ser Ser Ser Ser Gly His
785                 790                 795                 800

Ser Gln Ser Thr Leu Phe Asp Ser Asp Val Phe Gln Thr Asn Asn Asn
                805                 810                 815

Glu Asn Pro Tyr Thr Asp Pro Ala Asp Leu Ile Ala Asp Ala Ala Gly
                820                 825                 830

Ser Pro Ser Ser Asp Ser Pro Thr Asn His Phe Phe His Asp Gly Val
                835                 840                 845

Asp Phe Asn Pro Asp Leu Leu Asn Ser Gln Ser Gln Ser Gly Phe Gly
                850                 855                 860

Glu Glu Tyr Phe Asp Glu Ser Ser Gln Ser Gly Asp Asn Asp Asp Phe
865                 870                 875                 880

Lys Gly Phe Ala Ser Gln Ala Leu Asn Thr Leu Gly Val Pro Met Leu
                885                 890                 895

Gly Gly Asp Asn Gly Glu Thr Lys Phe Lys Gly Asn Asn Gln Ala Asp
                900                 905                 910

Thr Val Asp Phe Ser Ile Ile Ser Val Ala Gly Lys Ala Leu Ala Pro
                915                 920                 925

Ala Asp Leu Met Glu His His Ser Gly Ser Gln Gly Pro Leu Leu Thr
930                 935                 940

Thr Gly Asp Leu Gly Lys Glu Lys Thr Gln Lys Arg Val Lys Glu Gly
945                 950                 955                 960

Asn Gly Thr Ser Asn Ser Thr Leu Ser Gly Pro Gly Leu Asp Ser Lys
                965                 970                 975

Pro Gly Lys Arg Ser Arg Thr Pro Ser Asn Asp Gly Lys Ser Lys Asp
                980                 985                 990

Lys Pro Pro Lys Arg Lys Lys Ala  Asp Thr Glu Gly Lys  Ser Pro Ser
                995                 1000                1005

His Ser  Ser Ser Asn Arg Pro  Phe Thr Pro Pro Thr  Ser Thr Gly
     1010                 1015                1020

Gly Ser  Lys Ser Pro Gly Ser  Ala Gly Arg Ser Gln  Thr Pro Pro
     1025                 1030                1035
```

-continued

```
Gly Val Ala Thr Pro Pro Ile Pro Lys Ile Thr Ile Gln Ile Pro
    1040                1045                1050

Lys Gly Thr Val Met Val Gly Lys Pro Ser Ser His Ser Gln Tyr
    1055                1060                1065

Thr Ser Ser Gly Ser Val Ser Ser Ser Gly Ser Lys Ser His His
    1070                1075                1080

Ser His Ser Ser Ser Ser Ser Ser Ser Ala Ser Thr Ser Gly Lys
    1085                1090                1095

Met Lys Ser Ser Lys Ser Glu Gly Ser Ser Ser Lys Leu Ser
    1100                1105                1110

Ser Ser Met Tyr Ser Ser Gln Gly Ser Ser Gly Ser Ser Gln Ser
    1115                1120                1125

Lys Asn Ser Ser Gln Ser Gly Gly Lys Pro Gly Ser Ser Pro Ile
    1130                1135                1140

Thr Lys His Gly Leu Ser Ser Gly Ser Ser Ser Thr Lys Met Lys
    1145                1150                1155

Pro Gln Gly Lys Pro Ser Ser Leu Met Asn Pro Ser Leu Ser Lys
    1160                1165                1170

Pro Asn Ile Ser Pro Ser His Ser Arg Pro Pro Gly Gly Ser Asp
    1175                1180                1185

Lys Leu Ala Ser Pro Met Lys Pro Val Pro Gly Thr Pro Pro Ser
    1190                1195                1200

Ser Lys Ala Lys Ser Pro Ile Ser Ser Gly Ser Gly Gly Ser His
    1205                1210                1215

Met Ser Gly Thr Ser Ser Ser Gly Met Lys Ser Ser Ser Gly
    1220                1225                1230

Leu Gly Ser Ser Gly Ser Leu Ser Gln Lys Thr Pro Pro Ser Ser
    1235                1240                1245

Asn Ser Cys Thr Ala Ser Ser Ser Ser Phe Ser Ser Ser Gly Ser
    1250                1255                1260

Ser Met Ser Ser Ser Gln Asn Gln His Gly Ser Ser Lys Gly Lys
    1265                1270                1275

Ser Pro Ser Arg Asn Lys Lys Pro Ser Leu Thr Ala Val Ile Asp
    1280                1285                1290

Lys Leu Lys His Gly Val Val Thr Ser Gly Pro Gly Gly Glu Asp
    1295                1300                1305

Pro Leu Asp Gly Gln Met Gly Val Ser Thr Asn Ser Ser Ser His
    1310                1315                1320

Pro Met Ser Ser Lys His Asn Met Ser Gly Gly Glu Phe Gln Gly
    1325                1330                1335

Lys Arg Glu Lys Ser Asp Lys Asp Lys Ser Lys Val Ser Thr Ser
    1340                1345                1350

Gly Ser Ser Val Asp Ser Ser Lys Lys Thr Ser Glu Ser Lys Asn
    1355                1360                1365

Val Gly Ser Thr Gly Val Ala Lys Ile Ile Ser Lys His Asp
    1370                1375                1380

Gly Gly Ser Pro Ser Ile Lys Ala Lys Val Thr Leu Gln Lys Pro
    1385                1390                1395

Gly Glu Ser Ser Gly Glu Gly Leu Arg Pro Gln Met Ala Ser Ser
    1400                1405                1410

Lys Asn Tyr Gly Ser Pro Leu Ile Ser Gly Ser Thr Pro Lys His
    1415                1420                1425
```

```
Glu Arg Gly Ser Pro Ser His Ser Lys Ser Pro Ala Tyr Thr Pro
    1430                1435                1440

Gln Asn Leu Asp Ser Glu Ser Glu Ser Gly Ser Ser Ile Ala Glu
    1445                1450                1455

Lys Ser Tyr Gln Asn Ser Pro Ser Ser Asp Asp Gly Ile Arg Pro
    1460                1465                1470

Leu Pro Glu Tyr Ser Thr Glu Lys His Lys Lys His Lys Lys Glu
    1475                1480                1485

Lys Lys Lys Val Lys Asp Lys Asp Arg Asp Arg Asp Arg Asp Lys
    1490                1495                1500

Asp Arg Asp Lys Lys Lys Ser His Ser Ile Lys Pro Glu Ser Trp
    1505                1510                1515

Ser Lys Ser Pro Ile Ser Ser Asp Gln Ser Leu Ser Met Thr Ser
    1520                1525                1530

Asn Thr Ile Leu Ser Ala Asp Arg Pro Ser Arg Leu Ser Pro Asp
    1535                1540                1545

Phe Met Ile Gly Glu Glu Asp Asp Asp Leu Met Asp Val Ala Leu
    1550                1555                1560

Ile Gly Asn
    1565

<210> SEQ ID NO 3
<211> LENGTH: 26
<212> TYPE: DNA
<213> ORGANISM: Artificial
<220> FEATURE:
<223> OTHER INFORMATION: The artificial sequence is a nucleic acid.

<400> SEQUENCE: 3
aattcagaca tgcctagaca tgcctg                                          26

<210> SEQ ID NO 4
<211> LENGTH: 15
<212> TYPE: PRT
<213> ORGANISM: Artificial
<220> FEATURE:
<223> OTHER INFORMATION: The artificial sequence is a nucleic acid.

<400> SEQUENCE: 4

Pro Leu Ser Gln Glu Thr Phe Ser Asp Leu Trp Lys Leu Leu Pro
1               5                   10                  15

<210> SEQ ID NO 5
<211> LENGTH: 29
<212> TYPE: DNA
<213> ORGANISM: Artificial
<220> FEATURE:
<223> OTHER INFORMATION: The artificial sequence is a nucleic acid.

<400> SEQUENCE: 5
agggatccgt atcttttcag caccctgtg                                       29

<210> SEQ ID NO 6
<211> LENGTH: 32
<212> TYPE: DNA
<213> ORGANISM: Artificial
<220> FEATURE:
<223> OTHER INFORMATION: The artificial sequence is a nucleic acid.

<400> SEQUENCE: 6
aggaattctc acttcatgcc agagcttgaa ct                                   32
```

```
<210> SEQ ID NO 7
<211> LENGTH: 20
<212> TYPE: DNA
<213> ORGANISM: Artificial
<220> FEATURE:
<223> OTHER INFORMATION: The artificial sequence is a nucleic acid.

<400> SEQUENCE: 7
cagtaatagt actctctcgg                                               20

<210> SEQ ID NO 8
<211> LENGTH: 28
<212> TYPE: DNA
<213> ORGANISM: Artificial
<220> FEATURE:
<223> OTHER INFORMATION: The artificial sequence is a nucleic acid.

<400> SEQUENCE: 8
aggaattcta agcccttctc cactactt                                      28

<210> SEQ ID NO 9
<211> LENGTH: 26
<212> TYPE: DNA
<213> ORGANISM: Artificial
<220> FEATURE:
<223> OTHER INFORMATION: The artificial sequence is a nucleic acid.

<400> SEQUENCE: 9
aattcagaca tgcctagaca tgcctg                                        26

<210> SEQ ID NO 10
<211> LENGTH: 35
<212> TYPE: DNA
<213> ORGANISM: Artificial
<220> FEATURE:
<223> OTHER INFORMATION: The artificial sequence is a nucleic acid.

<400> SEQUENCE: 10
tatgtctaag ggacctgcgg ttggcattga tcttg                              35
```

P53 REGULATORY PROTEIN CALLED RB18A AND USES THEREOF

The present invention relates to a new protein called RB18A for "Recognized By PAb1801 moAntibody", which is a p53 regulatory protein, to the nucleotide sequence encoding said protein, and to the diagnostic and therapeutic applications thereof.

The p53 protein plays an important and complex role in cells. In normal cells, wild-type p53 is involved in genome stability (Lane, 1992) and in reparation of DNA lesions (Kastan et al., 1991; Kastan et al., 1992; Fritsche et al., 1993). In tumor cells, overexpression of wild-type p53 induces, depending on cell type. a G1 cell-cycle growth arrest (Ginsberg et al., 1991; Mercer et al., 1991) or apoptosis in vitro (Yonish-Rouache et al., 1991; Johnson et al., 1993) and in vivo (Shaw et al., 1992; Radinsky et al., 1994). These functions of p53 are related to its property to transactivate (Kastan et al., 1992; Scharer and Iggo, 1992; El-Deiry et al., 1993) or to repress transcription of different genes (Ginsberg et al., 1991; Santhanam et al., 1991; Subler et al., 1992) and to inhibit cellular DNA replication (Miller et al., 1995; Cox et al., 1995).

The regulatory functions of p53 are associated to specific domains (Soussi et al., 1990). Its N-terminal domain acts as a trans-activation domain (Fields and Jang, 1990; O'Rourke et al., 1990; Raycroft et al., 1990). Its central domain contains a sequence-specific DNA binding site (Wang et al., 1993; Pavietich et al., 1993; Bargonetti et al., 1993), which interacts with two copies of the 10 bp sequence 5'-PuPuPuC(A/T)(T/A)GPyPyPy-3', separated by up to 13 bp (El-Deiry et al., 1992; Funk et al., 1992). This DNA element is present in promotor of several genes including WAF1 (El-Deiry et al., 1993), GADD45 (Kastan et al., 1992), the muscle creatine kinase gene (Weintraub et al., 1991), and the MDM2 gene (Barak et al., 1993). Other domains modulate the specific interaction of p53 with DNA. Indeed, a tetramerisation domain localized within the C-terminal stabilizes this interaction (El-Deiry et al., 1992; Funk et al., 1992; Arrowsmith and Morin, 1996). In addition, the p53 C-terminal domain contains a negative autoregulation site of sequence-specific DNA binding (Hupp et al., 1992). The C-terminal domain also carries a nonspecific DNA binding activity (Wang et al., 1993). This property has been associated to a DNA annealing and strand-transfer activities of p53 (Reed et al., 1995).

Thus, proteins which interact with one of these p53 domains should regulate p53 functions. Different proteins have been described as interacting with p53: viral SV40 large T antigen (Lane and Crawford, 1979), adenovirus ElB 55K (Sarnow et al., 1982), EBV BZLFI (Zhang et al., 1994), cellular Hsp70 (Pinhasi-Kimhi, 1986), MDM2 (Mommand et al., 1992), TBP (Seto et al., 1992), WT1 (Maheswaran et al., 1993), the Epstein-Barr virus/C3d receptor (CR2, CD21) (Barel et al., 1989) and more recently PACT (Simons et al., 1997). WO 95/14777 also discloses p53-binding polypeptides, called WBPI and p53UBC. Furthermore, monoclonal antibodies (moAb) directed against specific p53 domains are also p53 binding proteins which allow to analyze the role of p53 domains and to distinguish between wild-type or mutant p53 forms. PAb1620 moAb specifically recognized a conformational epitope only expressed on wild-type p53 (Milner et al., 1987), while PAb240 moAb recognized a sequencial epitope localized in the central region of p53 and demasked only on mutated p53 (Gannon et al., 1990). Other anti-p53 moAb as PAb1801 (binding to aminoacids 46 to 55 of p53) and DO1 (binding to aminoacids 21 to 25 of p53) or PAb421 (binding to aminoacids 371 to 380 of p53) were found to be directed against either the N or the C terminal domains of the p53 protein, respectively (Legros et al., 1994). PAb421 moAb activates the sequence-specific DNA binding activity of p53, in a similar manner to phosphorylation or binding of bacterial Hsp70(dnak) on the p53 C-terminal domain (Hupp et al., 1992).

The authors of the present invention have now identified a new cellular protein, with an apparent molecular weight of 205 kDa. This protein was called RB18A for "Recognized By PAb1801 moAb", as isolated after immunological screening of a cDNA expression library using the specific anti-p53 moAb (monoclonal antibody), PAb1801. Although no significant homology has been found with p53 at the level of nucleotide or deduced-protein sequence, RB18A protein shared some antigenic epitopes with p53 as recognized by different anti-p53 moAbs. Furthermore, RB18A protein shares some identical functional properties with the p53 protein, i.e. DNA-binding, homo-oligomerization, binding to p53 and activation of the sequence specific DNA binding function of p53.

In the instant application,

SEQ ID n°1 represents the cDNA sequence encoding the human RB18A protein.

SEQ ID n°2 represents the aminoacid sequence of the human RB18A protein.

The fragments of the human RB18A protein of interest are the following:

- the aminoacid fragment from aminoacid 436 to aminoacid 1566, encoded by the nucleotide fragment from nucleotide 1541 to nucleotide 4933;
- the aminoacid fragment from aminoacid 436 to aminoacid 1228, encoded by the nucleotide fragment from nucleotide 1541 to nucleotide 3919;
- the aminoacid fragment from aminoacid 436 to aminoacid 927, encoded by the nucleotide fragment from nucleotide 1541 to nucleotide 3014;
- the aminoacid fragment from aminoacid 1537 to aminoacid 1566, encoded by the nucleotide fragment from nucleotide 4846 to nucleotide 4933;
- the aminoacid fragment from aminoacid 1234 to aminoacid 1566, encoded by the nucleotide fragment from nucleotide 3935 to nucleotide 4933;
- the aminoacid fragment from aminoacid 1234 to aminoacid 1406, encoded by the nucleotide fragment from nucleotide 3935 to nucleotide 4453, which represents the p53 binding and homo-oligomerization domains;
- the aminoacid fragment from aminoacid 927 to aminoacid 1406, encoded by the nucleotide fragment from nucleotide 3014 to nucleotide 4453, which represents the DNA binding domain.

A subject of the present invention is thus an isolated nucleic acid comprising a sequence selected from the group consisting of a fragment from nucleotide 1541 to nucleotide 4933 of SEQ ID n°1, a fragment from nucleotide 1541 to nucleotide 3919 of SEQ ID n°1, a fragment from nucdeotide 1541 to nucleotide 3014 of SEQ ID n°1, a fragment from nucleotide 4846 to nucleotide 4933 of SEQ ID n°1, a fragment from nucleotide 3935 to nucleotide 4933 of SEQ ID n°1, a fragment from nucleotide 3935 to nucleotide 4453 of SEQ ID n°1, a fragment from nucleotide 3014 to nucleotide 4453 of SEQ ID n°1, and a homologous nucleic acid sequence thereof.

More particularly the present invention relates to an isolated nucleic acid having a sequence selected from SEQ ID n°1, and a homologous nucleic acid sequence thereof.

"A homologous nucleotide sequence" is understood as meaning a sequence which differs from the sequences to which it refers by mutation, insertion, deletion or substitution of one or more bases.

Preferably, such homologous sequences show at least 70% of homology, preferably 80% of homology, more preferably 90% of homology with SEQ ID n° 1 or fragments thereof, as above defined.

A polynucleotide of the invention, having a homologous sequence, hybridizes to the sequences to which it refers, preferably under stringent conditions. Parameters that define the conditions of stringency depend upon the temperature at which 50% of annealed strands separate ($T_m$).

For sequences comprising more than 30 nucleotides, $T_m$ is calculated as follows:

$T_m$=81.5+0.41(% $G+C$)+16.6 Log (positive ion concentration)−0.63(% formamide)−(600/polynucleotide size in base pairs)(Sambrook et al, 1989).

For sequences comprising less than 30 nucleotides, $T_m$ is calculated as follows:

$T_m$=4($G+C$)+2($A+T$).

Under appropriate stringent conditions avoiding the hybridization of non specific sequences, hybridization temperature is around from. 5° C. to 30° C., preferably from 5° C. to 10° C. below the calculated $T_m$, and hybridization buffer solutions that are used are preferably solutions with high ionic strength, such as an aqueous 6×SSC solution for example.

A nucleotide sequence homologous to SEQ ID n° 1 means a nucleotide sequence which differs from SEQ ID n° 1 by mutation, insertion, deletion or substitution of one or more bases, or by the degeneracy of the genetic code so long as it codes for a polypeptide having the biological activity of RB18A protein, as defined below.

Said homologous sequences include mammalian genes coding for the RB18A protein, preferably of primate, cattle, sheep, swine, or rodent, as well as allelic variants.

Polynucleotides of the invention are useful as probes for nucleic acid hybridization to detect the transcription rate and abundance of RB18A mRNA in individual lymphocytes (or other cell types), for example by in situ hybridization, and in specific cell populations for example by Northern Blot analysis and/or by in situ hybridization (Alwine et al., (1977)) and/or PCR amplification and/or LCR detection. Such nucleic acid hybridization probes have utility for in vitro screening methods for therapeutic agents (e.g., antineoplastic agents), for diagnosis and treatment of neoplastic or preneoplastic pathological conditions and genetic diseases.

A subject of the present invention is also a nucleic acid sequence which specifically hybridizes with a nucleic acid sequence of the invention as previously defined, or with their complementary sequences.

"A sequence which specifically hybridizes [. . . ]" is understood as meaning a sequence which hybridizes with the sequences to which it refers under the conditions of high stringency (Sambrook et al, 1989).

Such sequences can be oligonucleotides which are particularly useful as primers or probes. In that case their sequences have preferably at least 15, and more preferably at least 20 bases.

Such sequences can also be anti-sense polynucleotides. In that case their sequences have preferably the full length of the cDNA sequence coding for RB18A.

Such antisense polynucleotides are employed to inhibit transcription and/or translation of the RB1 8A mRNA species and thereby effect a reduction in the amount of the respective RB18A polypeptide in a cell (e.g., a lymphocytic leukemia cell of a patient). Such antisense polynucleotides can function as p53-modulating agents by inhibiting the formation of RB18A required for modulation of p53 function by RB18A.

In a variation of the invention, polynucleotides of the invention are employed for diagnosis or treatment of pathological conditions or genetic disease that involve neoplasia or other pathological conditions related to p53 function, and more specifically conditions and diseases that involve alterations in the structure or abundance of RB18A.

The polynucleotide sequences of the invention may be fused, by polynucleotide linkage, in frame with another polynucleotide sequence encoding a different protein (e.g., glutathione S-transferase or β-galactosidase) for encoding expression of a fusion protein.

Polynucleotides of the invention can above all serve as templates for the recombinant expression of quantities of RB18A polypeptide.

A subject of the present invention is thus an isolated RB18A polypeptide substantially having the aminoacid sequence encoded by a nucleic acid sequence as above described.

More particularly the present invention relates to an isolated RB18A polypeptide or a fragment thereof comprising a sequence selected from the group consisting of a fragment from aminoacid 436 to aminoacid 1566 of SEQ ID n°2, a fragment from aminoacid 436 to aminoacid 1228 of SEQ ID n°2, a fragment from aminoacid 436 to aminoacid 927 of SEQ ID n°2, a fragment from aminoacid 1537 to aminoacid 1566 of SEQ ID n°2, a fragment from aminoacid 1234 to aminoacid 1566 of SEQ ID n°2, a fragment from aminoacid 1234 to aminoacid 1406 of SEQ ID n°2, a fragment from aminoacid 927 to aminoacid 1406 of SEQ ID n°2, and a homologous aminoacid sequence thereof.

A preferred polypeptide of the invention is an isolated RB18A polypeptide having the aminoacid sequence of SEQ ID n°2, or a homologous aminoacid sequence thereof.

"A homologous aminoacid sequence" is understood as meaning a sequence which differs from the sequences to which it refers by mutation, insertion, deletion or substitution of one or more aminoacids, without inducing substantial modification of biological and/or immunological properties. Said homologous aminoacid sequence shows at least 70% of homology, preferably 90% of homology with the RB18A polypeptide of SEQ ID n°2.

The "biological properties" of the polypeptides of the invention refer to the activity of the RB18A protein, such as DNA-binding, homo-oligomerization, binding to p53 and/or activation of the sequence specific DNA binding function of p53.

The "immunological properties" of the polypeptides of the invention refer to the ability of the polypeptides of the invention to induce an immunological response mediated by antibodies, such as PAb1801 moAb, which recognize the RB18A polypeptide of the invention.

Presence on RB18A protein of common antigenic determinants with the p53 protein was demonstrated as β-galactosidase-RB18A fusion proteins or in vitro translated products of RB18A cDNA were recognized by specific anti-p53 antibodies. This cross-reactivity was supported by binding on RB18A of anti-p53 moAb which reacted with 3 distinct domains of p53. Indeed, the epitopes recognized on p53 by anti-p53 moAb as DO-1, PAbl 801 and PAb421 are localized in its N or C terminal domains and are defined by aa sequence 21–25, 46–55 and 371–380, respectively (Legros et al., 1994). PAb1801, DO-1 moAb and a polyclonal anti-p53.1 Ab, prepared against the p53 N-terminal amino acid sequence 13–27, recognized the native RB18A protein. PAb421, directed against the p53 C-terminal domain, recognized only the SDS-treated form of RB18A protein. Absence of PAb421 interaction with native RB18A could be due to the masking of the PAb421 epitope in the protein core. It was also demonstrated that in vitro phosphorylation on PAb421 moAb epitope of murine (Milne et al., 1996) or human (Takenaka et al., 1995) p53 could occur in reticulocyte lysates and that these phosphorylations inhibited PAb421 moAb interaction with p53. This cross-reactivity was limited to the p53 N and C domains, as anti-p53 moAb reacting with the central domain of p53, as HO15-4, HO3-5, HO7-1, did not react with RB18A protein However, computer analysis of amino acid sequence of the primary structure of both proteins did not allow to localize any significant identity or homology between both RB18A and p53 protein sequences. This apparent discrepancy was more likely due to the presence on RB18A of epitopes common with p53 and expressed on the tertiary structure of native RB18A protein, also partially conserved in SDS-treated RB18A protein. Similar data were obtained by Stephen et al. (1995) who reported that moAbs, including anti-p53 moAb, with known peptide reactivity, selected from 12-mer and 20-mer phage-displayed libraries not only the expected peptides but also sequences with no discernible homology with the original antigen. Presence of epitopes defined as common antigenic determinants and characterized by no primary sequence homology has been previously mentionned and called "mimotopes" by Geisen et al (1986, 1987). Interaction of a specific moAb with both epitope and mimotope motifs was explained by interaction with the two different ligands either of distinct paratopes on the same moAb or alternative contacts of the same paratope (Stephen et al., 1995).

In addition, RB18A protein shared some identical properties with p53 protein: indeed, RB18A protein binds to DNA, seif-oligomerize and binds to p53. This was also supported by co-immunoprecipitation of p53 and RB18A on polyclonal anti-RB18A antibody. In addition, RB18A is able to activate the sequence specific binding of p53 to DNA. All these activities, which supported the functional homology between RB18A and p53 proteins, were associated to the C-terminal domain of RB18A protein, as for p53, and more specifically to the PAb421 binding site present in this domain. Indeed: a) the domain responsible for DNA binding activity and localized on aa 927–1406, was recognized by PAb421 moAb. Part of this domain is also responsible for the self-oligomerization of RB13A (aa 1234–1406); b) in opposite to the full length RB18A, deletion of the regions recognized by PAb421 moAb abolished RB18A activation of the p53 specific DNA binding activity; c) PAb421 also defined in p53 a motif able to activate the sequence specific binding of p53 to DNA. Jayaraman and Prives (1995) showed that the C-terminus of human p53 (aa 311–393) was able to activate in trans the latent activity of sequence specific DNA binding activity of p53. A polypeptide corresponding to the p53 amino acid sequence 311 to 367 did not induce this activation suggesting that the 26 C-terminus residues were crucial for this activity. This result was confirmed by Hupp et al. (1995) who found that small peptides carrying the PAb421 epitope also stimulated the DNA-binding activity of p53.

The possibility that PAb421 moAb may define a domain which bound to DNA and/or was responsible for oligomerization has been suggested by Daud et al. (1993) and Kim et al. (1996). Indeed, PAb421 moAb cross-reacted with the mouse RAD50 protein, homologous to the yeast RAD50 protein (Daud et al., 1993), whose expression was increased in response to DNA damage. RAD50 protein carries DNA-binding oligomerization (Daud et al., 1993; Raymond and Kleckner, 1993; Kim et al., 1996), as p53. Therefore, Kim et al. (1996) suggested that the common structural epitope recognized by PAb421 Moab could imply a functional homology between RAD50 and p53. Thus, PAb421 moAb could define a motif in a protein family, including RB18A, RAD50 and p53, which carried DNA-binding and oligomerisation domains. Demonstration that a moAb may define a functionally conserved epitope on two distinct proteins has been also suggested for PAb204, an anti-T-Ag moAb. Indeed, PAb204 reacted with T-Ag and with a p68 protein (Lane and Hoeffler, 1980), both proteins exhibiting RNA helicase activity (Ford et al., 1988; Hirling et al., 1989).

Furthermore, RB18A regulated p53 specific binding on his DNA consensus binding site. Absence of detectable amount of RB18A protein in the retarded band suggested that the activation of p53 binding on DNA by RB18A was induced through an unstable (and/or low affinity) interaction between both proteins. The unstable interaction of RB18A with p53 which activated its binding to DNA was similar to the unstable interaction of p53 C-terminal domain added in trans which activated the p53 binding to his cognate DNA binding site (Jayaraman and Prives, 1995). However, a stable (and/or higher affinity) interaction between GST-RB18A and wild-type or mutated p53 was shown in absence of specific p53 DNA binding sequence. Hupp et al. (1995) suggested that interaction of the C-terminal domain of one p53 molecule with distinct region of other p53 molecule locks p53 in an inactive form for DNA binding. Addition in trans of a C-terminal peptide could promote the dissociation of the C-terminal of the full length p53 from the other region of p53. Disruption of this inhibitory interaction would induce the conformational change required to activate the DNA binding of p53. Thus, RB18A could play the same role by interacting with p53, therefore promoting conformational change of p53 and demasking its sequence-specific DNA binding domain.

Altogether, these data demonstrated that RB18A protein, which carried common antigenic and functional properties with p53, is a new protein which could regulate p53 functions.

More particularly, the RB18A protein of the invention plays an important role in the native p53 stabilization. In the absence of RB18A, native p53 has a short half-life time and consequently is hardly detected, whereas mutated p53 polypeptides are more easily detected. In the presence of RB18A, one can detect a higher level of native p53 polypeptides, due to either a stabilization of native p53 or a transformation of mutated p53 into functional p53.

Furthermore, by activating p53 and interacting with DNA non specific sequences, the RB18A polypeptide of the invention blocks the G1 phase of the cell cycle and/or regulates apoptosis. The RB18A polypeptides of the invention are thus highly interesting for controlling cell growth and apoptose, which makes them good candidates mainly for antineoplastic therapy.

On the other hand, the gene coding for the RB18A polypeptide may be induced by DNA alterations which are provoked by mutagenic agents such as UV-ray, X-ray, or chemotherapeutic agents for example. This induction would account for the failure of antineoplastic therapy using such mutagenic agents, in certain patient with a non-functional p53 (mutated and/or non-inducible p53 gene). The polypeptides or the polynucleotides of the invention could help to control this phenomenon and be used as therapeutic agents in said patients.

Besides its role in the p53 stabilization and activation, the RB18A polypeptide of the invention is also implicated in the DNA reparation by interacting with nuclear factors (e.g RXR) and helicases.

The authors of the present invention have also shown that the RB18A protein induces a reassociation of DNA double strands. In therapy, one can choose to either enhance or inhibit this renaturation. These different strategies depend on the type of cell which is targeted: tumor cells, or normal cells in a patient with cancer, after a surgery operation or after a therapy with mutagenic agents. They also depend on the type of tumor, as the cell cycle and the RB18A protein may be differently affected according to the type of tumor.

By using the FISH Mapping technique, the authors of the present invention have located the gene locus of RB18A on the chromosomal region 17q21. RB18A is thus a good candidate for preventing and/or treating diseases associated with a mutation or a loss in this region.

More particularly, as this region 17q21 also contains important genes, e.g. BRCA1, involved in the development of tumors, such as colon, breast or ovarian cancers, RB18A is expected to act as a tumor suppressor gene and to be useful for preventing and/or treating such tumors.

The polypeptides according to the invention can be obtained by any of the standard methods of purification of soluble proteins, by peptide synthesis or by genetic engineering. Said techniques comprise the insertion of a nucleic acid sequence coding for a peptide of the invention into an expression vector, such as a plasmid, and the transformation of host cells with the expression vector, by any of the methods available to the skilled person, like for instance electroporation.

The present invention thus relates to vectors for cloning and/or expression comprising a nucleic acid sequence of the invention and to host cell transfected with these vectors. The expression vector according to the invention comprises a nucleic acid sequence encoding a polypeptide of the invention, operably linked to elements allowing its expression. Such elements may be a promoter sequence, signals for initiation and termination of translation, as well as appropriate regions for regulation of translation. The insertion of said vector into the host cell may be transient or stable. Said vector may also contain specific signals for secretion of the translated protein.

These various control signals are selected according to the host cell which may be inserted into vectors which self-replicate in the selected host cell, or into vectors which integrate the genome of said host.

Host cells may be prokaryotic or eukaryotic, including but not limiting to bacteria, yeasts, insect cells, mammalian cells, including cell lines which are commercially available.

A subject of the present invention is also a method for producing a recombining RB18A polypeptide, wherein said host cell is transfected with said expression vector and is cultured in conditions allowing the expression of a polypeptide according to the invention.

Besides their use for regulating p53 protein and hence their application in the control of cell proliferation, the recombinant polypeptides of the invention are also useful for in vitro screening methods for therapeutic agents (e.g., antineoplastic agents), for diagnosis and treatment of neoplastic or preneoplastic pathological conditions and genetic diseases.

In one embodiment, candidate therapeutic agents are identified by their ability to block or increase the binding of RB18A to a p53 poiypeptide. The p53 polypeptide preferably is a full-length mature p53 protein and frequently is phosphorylated, although the phosphorylation state of individual p53 species can be variable. Typically, the p53 polypeptide comprises an amino acid sequence identical to a wild-type p53 protein sequence, although mutant p53 polypeptides are sometimes used if the mutant p53 polypeptide binds to the RB18A protein under control assay conditions (e.g., physiological conditions). Agents are tested for their ability to alter or augment binding between a p53 polypeptide and a RB18A polypeptide under suitable assay binding conditions. One means for detecting binding of a p53 polypeptide to a RB18A polypeptide is to immobilize the p53 polypeptide, such as by covalent or noncovalent chemical linkage to a solid support, and to contact the immobilized p53 polypeptide with a RB18A polypeptide that has been labelled with a detectable marker (e.g., by incorporation of radiolabelled amino acid, by epitope tagging and reporting with a fluorescent-labelled anti-epitope tag antibody, and the like). Such contacting is typically performed in aqueous conditions which permit binding of a p53 polypeptide to a RB18A polypeptide comprising a functional p53 binding site. Binding of the labelled RB18A polypeptide to the immobilized p53 is measured by determining the extent to which the labelled p53-interacting polypeptide is immobilized as a result of a specific binding interaction. Such specific binding may be reversible, or may be optionally irreversible if a cross-linking agent is added in appropriate experimental conditions. Alternatively, the p53 polypeptide may be labelled and the RB18A polypeptide immobilized. In one variation, the binding assay is performed with soluble (i.e., non-immobilized) p53 and RB18A polypeptides and the resultant bound complexes (p53:RB18A) are separated from unbound p53 and RB18A polypeptides, and the bound complexes are quantitated. Agents that inhibit or augment the formation of bound complexes as compared to a control binding reaction lacking agent are thereby identified as p53-modulating agents and are candidate therapeutic agents.

In one variation, the binding assay is performed in vivo in a cell, such as a yeast cell (e.g., Saccharomyces), and agents which inhibit or augment intermolecular complex between a p53 protein and a RB18A polypeptide are identified as p53-modulating agents. Frequently, the in vivo screening assay is a yeast two-hybrid system wherein the yeast cells express: (1) a first fusion protein comprising p53 and a first transcriptional regulatory protein sequence (e.g, GAL4 activation domain), (2) a second fusion protein comprising a RB18A polypeptide and a second transcriptional regulatory protein sequence (e.g., GAL4 DNA-binding domain), and (3) a reporter gene (e.g.,β-galactosidase) which is transcribed when an intermolecular complex comprising the first fusion protein and the second fusion protein is formed. If a functional p53:RB18A complex forms, the cell expresses the reporter gene which can be detected. Agents which inhibit or augment formation of functional p53:RB18A complexes (and thus reporter gene expression) are thereby identified as p53-modulating agents.

A subject of the present invention is a composition comprising polynucleotides encoding (1) a first hybrid polypeptide comprising a p53 polypeptide and an activator domain of a transcriptional activator protein, (2) a second hybrid polypeptide comprising a RB18A polypeptide, and a DNA-binding domain of said transcriptional activator protein, and (3) a reporter polynucleotide linked to a transcriptional regulatory element whose transcriptional activity is dependent upon the presence or absence of a heterodimer comprised of the first and second hybrid polypeptide.

A further subject of the present invention is a method for identifying agents that inhibit or augment binding of a p53 polypeptide to a RB18A polypeptide to form heteromultimers, said method comprising the steps of:

performing a heterodimerization assay which includes a p53 polypeptide species comprising a binding domain with a RB18A polypeptide species comprising a binding domain and an agent under suitable binding conditions;

determining whether the agent inhibits or augments heterodimerization of the p53 polypeptide to the RB18A polypeptide;

identifying agents which inhibit or augment said heterodimerization as candidate p53 modulating agents and candidate pharmaceuticals.

A still further subject of the invention is an agent that inhibits or augments binding of a p53 polypeptide to a RB18A polypeptide as identified by the above method, as well as a pharmaceutical composition comprising such an agent in association with a pharmaceutical acceptable carrier.

The present invention also relates to monoclonal or polyclonal antibodies, or fragments thereof, or chimeric or immunoconjugate antibodies, which are capable of specifically recognizing a polypeptide according to the invention.

Polyclonal antibodies can be obtained from serum of an animal immunized against RB18A, which can be produced by genetic engineering for example, as above described, according to standard methods well-known by one skilled in the art.

Monoclonal antibodies can be obtained according to the standard method of hybridoma culture (Kohler and Milstein, 1975).

The antibodies of the present invention can be chimeric antibodies, humanized antibodies, or antigen binding fragments Fab and F(ab')2. They can also be immunoconjugated or labelled antibodies.

More preferred are antibodies which are directed against the C-terminal part of RB18A.

Said antibodies are particularly useful for detecting or purifying a RB18A polypeptide according to the invention in a biological sample.

Various uses of such antibodies are to diagnose and/or stage neoplasms or other cell proliferation disease states, and for therapeutic application (e.g., as cationized antibodies or by targeted liposomal delivery) to treat neoplasia, inflammation, wound healing, graft rejection, and the like.

They can be used as diagnostic reagents to identify cells exhibiting altered p53 function (e.g., preneoplastic or neoplastic cells) in a cellular sample from a patient (e.g., a lymphocyte sample, a solid tissue biopsy) as being cells which contain an increased amount of RB18A as compared to non-neoplastic cells of the same cell type(s). Additionally, anti-RB18A antibodies may be used therapeutically by targeted delivery to neoplastic cells (e.g., by cationization or by liposome/immunoliposome delivery).

Furthermore, the RB18A polypeptide is likely to interact with helicases of infectious agents such as a virus, with an affinity superior to the interaction with cellular helicases, leading to inhibition of viral infection. Consequently, the anti-RB18A antibodies of the invention could serve as an indirect marker of an undetermined viral infection.

The present invention also relates to a method for screening RB18A mutants, comprising the steps of:

providing RB18A derivative polypeptides, wherein a RB18A "derivative polypeptide" means a polypeptide which differs from an isolated RB18A polypeptide of the invention by mutation, insertion, deletion or substitution of one or more aminoacids, without inducing substantial modification of biological and immunological properties;

testing said RB18A polypeptides for their binding affinity to native p53 protein and/or helicases of infectious agents;

identifying RB18A derivative polypeptides which bind to native p53 protein and/or helicases of infectious agents with an affinity superior to the isolated RB18A polypeptide of the invention, as RB18A mutants of interest.

Such RB18A mutants are good candidate for preventing and/or treating a disease involving p53 and/or an infection.

The present invention also encompasses a pharmaceutical composition comprising a RB18A mutant identified by the above method, in association with a pharmaceutically acceptable carrier.

Another subject of the present invention is a pharmaceutical composition comprising a purified RB18A polypeptide of the invention and/or a homologous polypeptide thereof, or an isolated nucleic acid sequence encoding said polypeptides in association with a pharmaceutically acceptable carrier.

The nucleic acid sequences of the invention may be administered in a naked form or in association with transfection-facilitating agents. They are preferably inserted in an appropriate vector to facilitate its penetration into the cell according to standard methods well-known by those skilled in the art.

In a gene therapy strategy, they may be more particularly inserted in retrovirus in association with a promoter specific of tumor cells, leading to the apoptosis of tumor cells.

A further subject of the present invention is a pharmaceutical composition comprising an anti-sense sequence capable of specifically hybridizing with a nucleic acid sequence encoding said polypeptides, in association with a pharmaceutically acceptable carrier.

A still further subject of the present invention is a pharmaceutical composition comprising an antibody specifically directed against said polypeptides, in association with a pharmaceutically acceptable carrier.

The pharmaceutical compositions of the invention which comprise a purified RB18A polypeptide or an isolated nucleic acid sequence encoding said polypeptide are useful for preventing or treating a variety of human and veterinary diseases, such as neoplasia, inflammation, wound healing, graft rejection reperfusion injury, myocardial infarction, stroke, traumatic brain injury, neurodegenerative diseases, aging, ischemia, toxemia, infection, AIDS and hepatitis. Yet, they are preferably used as antineoplastic compositions, or as compositions directed against any other cell proliferation disease. They can be in particular advantageously used in the treatment of the colon, breast of ovarian cancer.

The pharmaceutical compositions of the invention may be administered to a mammal, preferably to a human, in need of a such treatment, according to a dosage which may vary widely as a function of the age, weight and state of health of the patient, the nature and severity of the complaint and the route of administration.

The appropriate unit forms of administration comprise oral forms such as tablets, gelatin capsules, powders, granules and oral suspensions or solutions, sublingual and buccal administration forms, subcutaneous, intramuscular, intravenous, intranasal or intraoccular administration forms and rectal administration forms.

A further subject of the present invention is a method of preventing and/or treating a disease involving the RB18A protein, such as neoplasms or other cell proliferation disease, which comprises administering to a subject in need of a such treatment an amount of a pharmaceutical composition as above defined effective to prevent and/or alleviate said disease.

The present invention is further illustrated by, but not limited to, the figures and the examples that follow.

LEGENDS TO FIGURES

FIG. 1: Immunological analysis of D9 product by different anti-p53 moAbs.

Part A: proteins from Raji cell extracts (lanes 1), bacterial extracts of D22, one of the eight p53 clones (A1, lanes 2) or D9 clone (A2, lanes 2) were analyzed by SDS-PAGE, transferred onto nitrocellulose sheets and detected with different anti-p53 moAbs.

Part B: immunoprecipitation of in vitro translated products of D9 (B1) or p53. H8 (B2) cDNAs by anti-p53 moAbs, rabbit anti-p53 serum (anti-p53.1) or non immune serum (NIS). The name of the moAb used is indicated above each lane. Position of expected products are indicated by arrows.

FIG. 2: Schematic representation of the RB18A CDNA.

Part A: D9 clone, which allowed to isolate the full length RB18A cDNA, was obtained after immunoscreening with the PAb1801 anti-p53 moAb of a Uni-Zap XR cDNA expression library made from Raji cell mRNA. A 800-base pair probe derived from the 5' end of this cDNA was used to screen a human heart cDNA library to obtain the 5' end of RB18A cDNA. Three additional clones were obtained (clones 9.6, 9.10 and 9.1). They overlapped in their 3' region with the 5' part of D9 clone. The coding region is indicated as an open box, while the untranslated regions are shown as solid lines. Some of the restriction sites are indicated, B: BamHI, E: ECoRI, N: NheI, P: PstI.

Part B: Northern analysis of different tissues. A blot containing 5 μg polyadenylated RNA from a variety of human tissues (as described in Material and Methods) was screened either with the 800-base pair probe derived from the 5' end of the D9 partial RB18A cDNA (upper panel) or with a human, actine probe, with two forms of 2 and 1.8 kb in heart and skeleton muscle, as expected (lower panel).

FIGS. 3A–3F: Nucleotide and deduced amino acid sequence of RB18A cDNA.

The amino acid sequence is shown in one-letter code. The putative NLS are underlined.

FIGS. 4.1 and 4.2: Immunoblot analysis of cellular RB18A protein.

Proteins solubilized from Raji cell (100 μg) were analyzed on 7.5% SDS-PAGE, transferred onto nitrocellulose sheets and detected with anti-RB18A polyclonal antibody (lane 1) or with a non immune serum (lane 2). Position of the molecular marker size is indicated.

FIG. 5: Double-stranded DNA-binding ability of RB18A.

Part A: effect of salt concentration on double-stranded DNA-binding ability of RB18A. Five μl of in vitro translated product of RB18A cDNA was incubated with DNA-cellulose at the indicated concentration of NaCl (mM) as described in Material and Methods. Proteins were analyzed on a 10% SDS-PAGE. Bound proteins were quantified by laser densitometry of the autoradiogram.

Part B: DNA-binding assay in presence of 100 mM NaCl using 5 μl of rabbit reticulocyte lysate programmed by RB18A, p53wt, or Luciferase cDNAs.

FIG. 6: Interaction of GST-RB18A with in vitro $^{35}$S-translated products of RB18A, luciferase, p53wt and mutated p53.

One μg of GST-RB18A (lanes 2, 5, 8, and 11) or GST alone (lanes 3, 6, 9, and 12) were incubated with 5 μl of rabbit reticulocyte lysate programmed by RB18A (lanes 2 and 3), luciferase (lanes 5 and 6), p53wt (lanes 8 and 9) and mutated p53 (lanes 11 and 12) cDNAs. In control, 10% of the different proteins (lanes 1, 4, 7 and 10) used in each in vitro binding assay were directly run in gel.

FIG. 7: Mapping of binding sites on RB18A.

Part A: shematic representation of the deletion mutants of GST-RB18A with their binding properties summarized on the right part of the figure. A number (1 to 5) was attributed to each mutant and number 6 represents GST alone.

Part B: mapping of the binding sites for PAb1801 and PAb421 moAbs. Immunoblot analysis of Raji cell extracts (lanes R), RB18A mutants (lanes 1 to 5) and GST (lanes 6) with PAb 801 (Bl) or PAb421 (B2) moAbs and anti-GST Ab (B3). Position of molecular marker size is indicated on the right part of the gel.

Part C: mapping of the domains involved in oligomerization and interaction with p53. Deletion mutants of RB18A (lanes 1 to 5) or GST (lane 6) were incubated with 5 μl of rabbit reticulocyte lysate programmed by RB18A (C1) or p53-H8 (C2) cDNAs. Bound proteins were eluted and run on a 7.5% (C1) or 10% (C2) SDS-PAGE. In control, standards representing 10% of each added protein were used (lanes S).

Part D: mapping of the DNA-binding sites on RB18A protein. RB18A mutants (lanes 1 to 5) or GST (lane 6) were incubated with double-stranded DNA-cellulose in presence of 100 mM NaCl. Bound proteins were eluted, run on a 10% SDS-PAGE and transferred to nitrocellulose sheets. Detection was performed using an anti-GST Ab. Position of molecular marker size is indicated on the right of the gel.

Part E: Schematic representation of the localization of the RB18A functional domains. The domain responsible for the activation of p53 specific DNA binding function was characterized in FIG. 8.

Figure 8A:
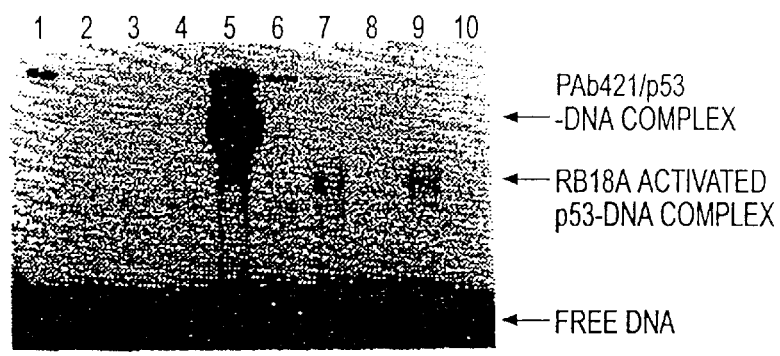
Figure 8B:
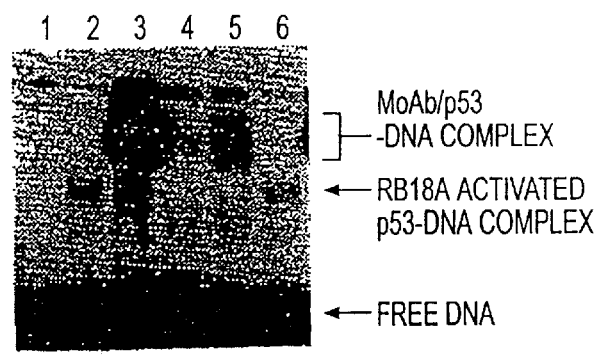

FIG. 8: Activation of p53 sequence specific DNA binding by the C-terminal domain of RB18A protein.

Part A: four pi of in vitro translated products of wild-type p53 (lanes 2, 5–10) or Luciferase (lanes 3–4) cDNAs were incubated for 20 min at room temperature with 0.2 μg of PAb421 (lane 5) or PAb1801 (lane 6) moAbs or with 1 μg of GST-RB18A-N2 (lanes 4, 7, 8 and 9) or GST-RB18A-NI1 (lane 10) proteins. Then, a radiolabeled oligonucleotide (0.4 ng per lane) containing the consensus DNA binding site of p53 was added for 20 min at 4° C. The specificity of the complex detected in lane 7 was determined by adding a 50×molar excess of unlabelled oligonucleotide either specific (lane 8) or nonspecific (lane 9) of p53 to the reaction mixture.

Part B: four μl of in vitro translated products of wild-type p53 (lanes 2–6) were pre-incubated for 20 min at room temperature with 1 μg of GST-RB18A-N2 protein. Then, the specific radiolabeled oligonucleotide (0.4 ng per lane) and PBS buffer (lane 2), 0.2 μg of PAb421 (lane 3), PAbI801 (lane 4) or DO-1 (lane 5) moAbs or 3 μg of anti-RB18A polyclonal antibodies (lane 6) were added for 20 min at 4° C. Complexes were run on a 4% acrylamide gel containing 0.4×TBE buffer. Positions of free DNA and specific complexes are indicated.

Figure 9:
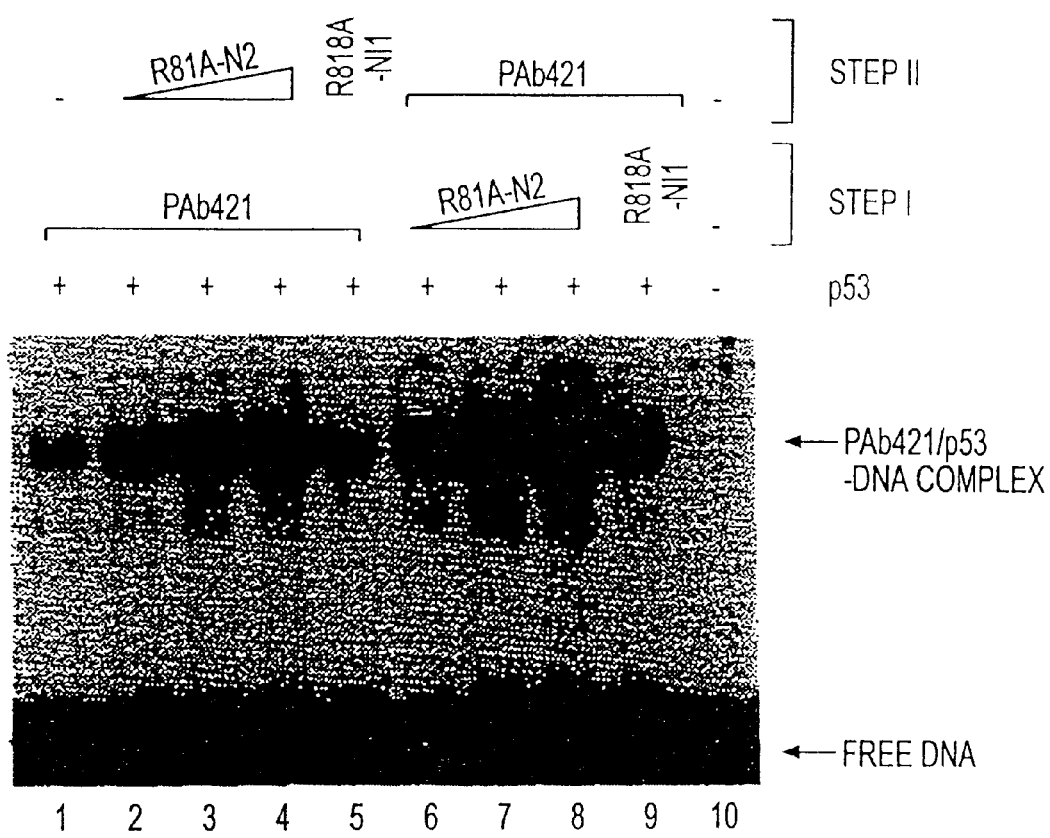

FIG. 9: The C-terminal domain of RB18A protein activates the p53 DNA binding in synergy with PAb421 moAb, in a dose-dependent manner.

Two μl of in vitro translated products of wild-type p53 were incubated for 20 min at room temperature in the first step either with 50 ng of PAb421 moAb (lanes 1–5) or increasing amounts of GST-RB18A-N2 protein (200 ng, 400 ng or 1 μg, lanes 6, 7 or 8 respectively) or with 1 μg GST-RB18A-Nil (lane 9). Then, in a second step, either increasing amounts of GST-RB18A-N2 (200 ng, 400 ng or 1 μg, lanes 2, 3 or 4 respectively) or 1 μg GST-RB18A-NI1 (lane 5) or 50 ng of Pab421 moAb (lanes 6 to 9) were added for 20 min at room temperature. Then, specific labelled p53 oligonucleotide was added in every lane for 20 min at 4° C. Complexes were run on a 4% acrylamide gel in 0.4×TBE buffer. Positions of free DNA and specific complex are indicated.

FIG. 10 : Annealing of complementary single-stranded nucleic acids by the carboxy-terminal domain of RB18A (A) or human wild-type p53 (B). The 194 bp fragment was obtained after digestion of DNA phage φx174 by HaeIII restriction enzyme and purification from gel, and was end-labelled with $\gamma^{32}$P-ATP. Radiolabelled ds DNA (1 ng) was heat denaturated and incubated for 25 min at 37° C. in 20 μl renaturation buffer (5 mM Tris pH 7.5, 10 mM KCl, 0.5 mM EDTA, 3.5% glycerol, 1.5 mM DTT, 1 mg/ml BSA) in presence of varying amounts of GST-RB18A-N2 (aa 1234–1566), His-Tag-wild type p53 or GST as indicated above each lane. Lanes A1 and B1 contain denaturated DNA without incubation at 37° C. (control ss), while lanes A2 and B2 contain the non denaturated DNA (control ds). Reactions were stopped by addition of 5 μl 5×stop buffer (0.85% SDS, 130 mM EDTA, 0.1% bromophenol blue, 20% glycerol). The ds and ss DNA products were separated on a 10% SDS-PAGE.

FIG. 11: Comparison of the rate of the annealing reaction promoted by the RB18A carboxy-terminal domain or by wild-type p53. Reactions were essentially made using the protocol described in legend of FIG. 1, except that reactions were stopped at the indicated time by addition of 5×stop buffer. The different proteins used in the annealing reaction mixtures at the indicated concentrations are: RB18A carboxy-terminal domain (aa 1234–1566) (■), 20 nM; wild-type p53 (→), 20 nM; lysozyme (o), 500 nM; no protein (•). Results were quantified by laser densitometry of the autoradiograms.

FIG. 12 : Carboxy-terminal domain of RB18A stimulates in vitro the DNA sequence specific binding of wild-type p53. A. In Vitro translation of cDNA encoding for wild-type p53 (p53-H8 cDNA provided by V. Rotter, Weizmann Institute of Science, Rehovot, Israel) (lane 1), or mutated p53-175H (provided by B. Vogelstein, Johns Hopkins University, Baltimore, USA) (lane 2) and p53-179Q (provided by 4. Baudier, INSERM U244, Grenoble, France) (lane 3). Translated products were obtained using the TNT-coupled reticulocyte lysate system (Promega) in presence of $^{35}$S-methionine (Amersham) and 5 μl were run on a 10% SDS-PAGE. B. Analysis of the DNA binding of wild-type or mutated p53 in presence of carboxy-terminal domain of RB18A. EMSA was carried out as described in example 5. The oligonucleotide probe containing the 20-mer p53 consensus DNA binding site (PG; Funk et al., 1992) with EcoRI-compatible ends is: 5'-AATTCAGACATGCCTAGACATGCCTG-3' (SEQ ID n°3). In vitro translated product (4 μl) of wild-type p53 (lanes 1–3), mutated p53-175H (lanes 4–6), or p53-179Q (lanes 7–9) were pre-incubated for 20 min at room temperature without (lanes 1, 4 and 7) or with 0.2 μg PAb421 moAb (lanes 2, 5 and 8), or 1 μg GST-RB18A-N2 (aa 1234–1566) (lanes 3, 6 and 9) in a final reaction volume of 14 pi buffer A (25 mM Tris, pH 7.4, 80 mM KCl, 0.1 mM EDTA, 1 mM DTT and 10% glycerol). Then, 6 μl buffer B (80 mM KCl, 16.6 mM MgCl$_2$ and 3 mg/ml BSA) containing 0.4 ng labeled oligonucleotide and 0.5 μg poly(dI-dC) were added and incubation was carried on for 20 min at 4° C. Reaction products were run for 15 min at 200 V on a 4% polyacrylamide gel in 0.4×Tris-Borate-EDTA buffer (90 mM Tris, 64.6 mM Borate, 2.5 mM EDTA, pH 8.3).

FIG. 13:

A. Carboxy-terminal domain of RB18A stimulates the transactivation by wild-type but not mutated p53. K562 human erythroid leukemia cells were maintained as suspension culture in RPMI containing 10% fetal calf serum (FCS). K562 cells (10.10$^6$) were mixed in 0.4 ml RPMI 1640 with 10 μg CAT reporter plasmid cloned downstream 13 repeats of PG element (PG$_{13}$-CAT; provided by B. Vogelstein) and with the indicated quantity of cDNAs of wild-type p53, p53-175H or RB18A (nucleotides 3935 to 4933) under the control of the cytomegalovirus (CMV) promoter. Then, cells were pulsed (1050 μF, 220 V) with a Easyject One apparatus (Eurogentec). After electroporation, cells were immediatly transferred in 5 ml RPMI 1640 containing 10% FCS and incubated at 37° C. in presence of 5% CO$_2$. CAT-Assay were performed at 24 h using the CAT enzyme assay system from Promega as described by the manufacturer. Assays were repeated 4 times and the result of a representative set of transfection is shown. B. Quantification by scintillation of experience presented in A using a β-counter.

EXAMPLE 1

Isolation of Clones Recognized by Anti-p53 moAbs

A. Materials and Methods

Cell Culture

Raji Burkitt B lymphoma cells were grown at 37° C. in RPMI 1640 medium supplemented with 10% (v/v) heat-inactived FCS in presence of 5% CO$_2$.

Antibodies

Monoclonal anti-p53 antibodies (moAbs) PAb1801 (aa 46–55), PAb421 (aa 371–380) and DO-1 (aa 21–25) were purchased from Oncogene Science. Other anti-p53 moAbs H07-1 (aa 291–300), HO3-5 (aa 181–190) and HO15-4 (aa 86(Legros et al., 1994) were provided by T. Soussi (Institut Curie, Paris, France). Polyclonal anti-peptide p53.1 and anti-RB18A antibodies were prepared by immunizing two rabbits every two weeks with 0.6 mg of synthetic peptide (aa 13–27 of the human p53, PLSQETFSDLWKLLP, SEQ ID n°4) covalently coupled to KLH (Pierce) or 30 μg of GST-RB18A-N1 fusion protein, respectively, in presence of Freund complete adjuvant for the first two immunisations and of Freund incomplete adjuvant for the last two immunisation. Rabbits were bled ten days after the last immunisation and presence of specific antibodies in the sera was tested on Raji cell extracts by Western blot.

Isolation of RB18A cDNA

A UniZAP-XR cDNA library was constructed from 5 μg polyadenylated RNA (Sambrook et al., 1989) using the ZAP-cDNA synthesis kit (Stratagene). The library contained a total of 2.10$^6$ pfu/ml and was amplified to a titer of 3.10$^9$ pfu/ml. Screening of 6.10$^5$ pfu was performed with PAb1801 moAb (0.2 μg/ml) in buffer containing 20 mM Tris, pH 7.5, 150 mM NaCl and 1% BSA. Goat anti-mouse Ab coupled to alkaline phosphatase (Dako) was used as the detection system for positive plaques and developped with BCIP/NBT reagents (Sigma). One clone (D9) containing the partial open reading frame of RB18A was retained. For the obtention of full-length RB18A cDNA, a $^{32}$P-labelled probe generated from the 5' end of D9 cDNA was used to screen a λgt11 human heart cDNA library (6.10$^5$ pfu) purchased from Clontech. A set of overlapping cDNAs was obtained. Sequencing was made in both directions using the T7 Sequenase polymerase sequencing kit (Amersham) with specific sequence primers.

Plasmids and Constructions

The plasmid pSP65-p53H8 encodes for the human wild-type p53 cDNA (Harris et al, 1986) (provided by V. Rotter, Weizmann Institute of Science, Rehovot, Israel), while the plasmid pGEM4-T1388 encodes a human p53 mutant with proline at position 273 (provided by J. Milner, University of York, York, England).

The GST-RB18A-N1 (aa 436 to 1566) fusion protein was obtained by cloning the D9 cDNA downstream of the glutathione transferase gene into the pGEX4T-3 vector (Pharmacia LKB). GST-RB18A-N2 (aa 1234 to 1566) was obtained by deleting the 5' sequence of D9 cDNA up to a BamHI (nt 3938) restriction site. A GST-RB18A-NI1 fusion protein, deleted in N-terminal and in central part of the protein, was obtained by digesting D9 cDNA with PstI restriction enzyme. The resulting protein is composed from amino acids 436 to 927 fusionned in frame with amino acids 1537 to 1566. Other fusion proteins were constructed using PCR fragments subcloned into the BamHI and EcoRI restriction sites of pGEX4T-3 vector. The GST-RB18A-NC1 (aa 436 to 1228) fusion protein was obtained using 5' primer 5'-AGGGATCCGTATCTTTTCAGCACCCTGTG-3' (SEQ ID n°5) (nt 1544) and 3' primer 5'-AGGATTCTCACTTCATGCCAGAGCTTGAACT-3' (SEQ ID n°6) (nt 3921) and the GST-RB18A-NC2 (aa 1234 to 1406) fusion protein using 5' primer 5'-CAGTAATAGTACTCTCTCGG-3' (SEQ ID n°7) (nt 3938) and 3' primer 5'-AGGAATTCTAAGCCCTTCTCCACTACTT-3' (SEQ ID n°8) (nt 4934).

In vitro Transcription/translation and Immunoprecipitation

Transcription and translation were performed with the TNT-coupled reticulocyte lysate system (Promega) in presence of $^{35}$S-methionine (Amersham) according to the manufacturer's instructions. For immunoprecipitation procedure, translation product (5 μl) was incubated for 90 min at 4° C. in 20 mM Tris (pH 7.4), 150 mM NaCl, 5 mM EDTA and 0.5% NP40 with 1 μg of the different moAbs bound to 15 μl protein G plus/protein A agarose (Oncogene Science) or with 50 μl rabbit sera bound to 10 mg Protein A sepharose (Pharmacia). Then, immunobeads were extensively washed. Bound proteins were eluted in sample buffer by heating for 3 min at 100° C. and analysed by 10% SDS-PAGE (Laemmli et al., 1970).

Western Immunoblotting

β-galactosidase fusion proteins were overproduced in transformed XL1-blue bacteria cells after a 3 hour-induction by 10 mM IPTG. Pelleted cells were boiled for 3 min in Laemmli sample buffer and proteins were analyzed on 10% SDS-PAGE. Immunoblotting was performed using different moAb or polyclonal Ab followed with peroxidase labelled secondary Ab(Barel et al., 1991).

B. Results

A UniZAP-XR cDNA expression library was prepared from polyadenylated RNA extracted from Raji human B lymphoma cells and was screened (6.10$^5$ plaque-forming units) with PAb1801, an anti-p53 moAb which specifically recognized the N-terminal domain of p53 (aa 46 to 55) (Legros et al., 1994). Sixteen positive phages were isolated and inserts were excised in vivo in pBluescript vector. Then, β-galactosidase fusion proteins were produced in *E. Coli* and immunoblotted with two anti-p53 moAbs, PAb1801 and PAb421, this latter reacting with the C-terminal domain of p53 (aa 371 to 380) (Legros et al., 1994). Nine clones producing fusion proteins recognized by these two anti-p53 moAbs were isolated. Among these clones, eight expressed the expected p53 molecule, as confirmed by partial cDNA sequencing, and are represented by D22 clone (FIG. 1A1). However, the ninth clone (D9) expressed a fusion protein characterized by an apparent molecular weight of 130 kDa (FIG. 1A2). D9 protein antigenicity towards anti-p53 Ab was also analyzed in immunoblotting or immunoprecipitation assays, on fusion protein or in vitro translated protein, respectively. D9 fusion protein was recognized by PAb1801 and PAb421 moAb (FIG. 1A2), while in vitro translated D9 protein (FIG. 1B1) was recognized by PAb1801, DO-1, another anti-p53 moAb, and by anti-p53.1, a polyclonal anti-p53 peptide serum but not by PAb421. Other anti-p53 moAb HO15-4, HO3-5, HO7-1, which recognized the p53 central region did not react with D9 clone product, in any assay. Thus, the protein encoded by the D9 cDNA presented common antigenic determinants with the N and C-terminal domains of p53.

EXAMPLE 2

Analysis of RB18A cDNA

A. Materials and Methods

Northern Blot Analysis

A blot containing 5 μg polyadenylated RNA from a variety of human tissues was purchased from Clontech and hybridized with the 800 bp probe derived from the 5' end of D9 cDNA.

B. Results

Figure 2B:
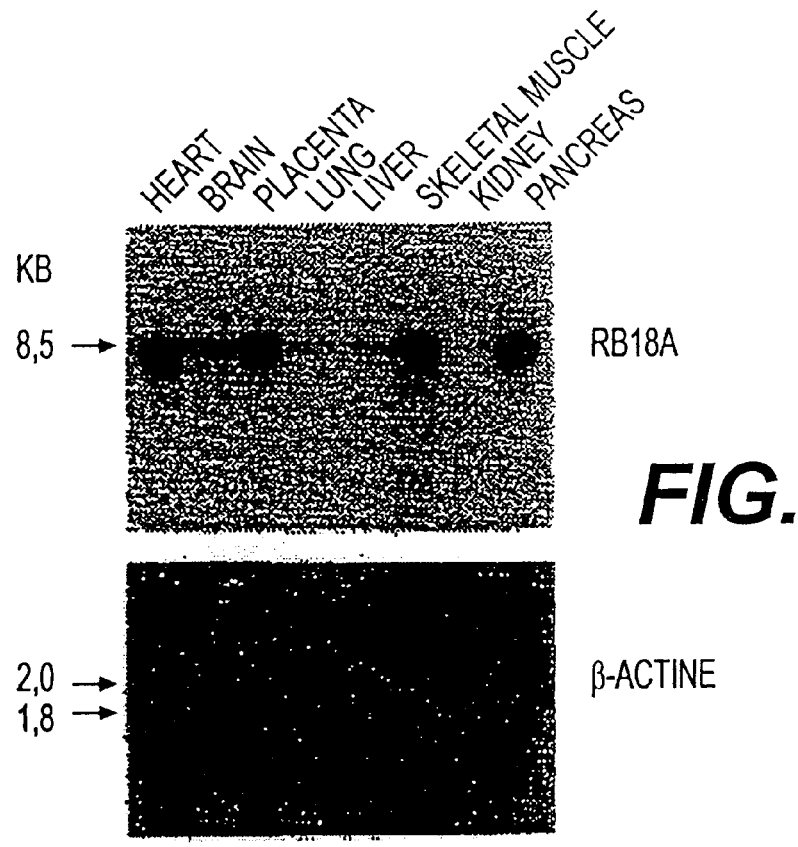
Figure 3A:
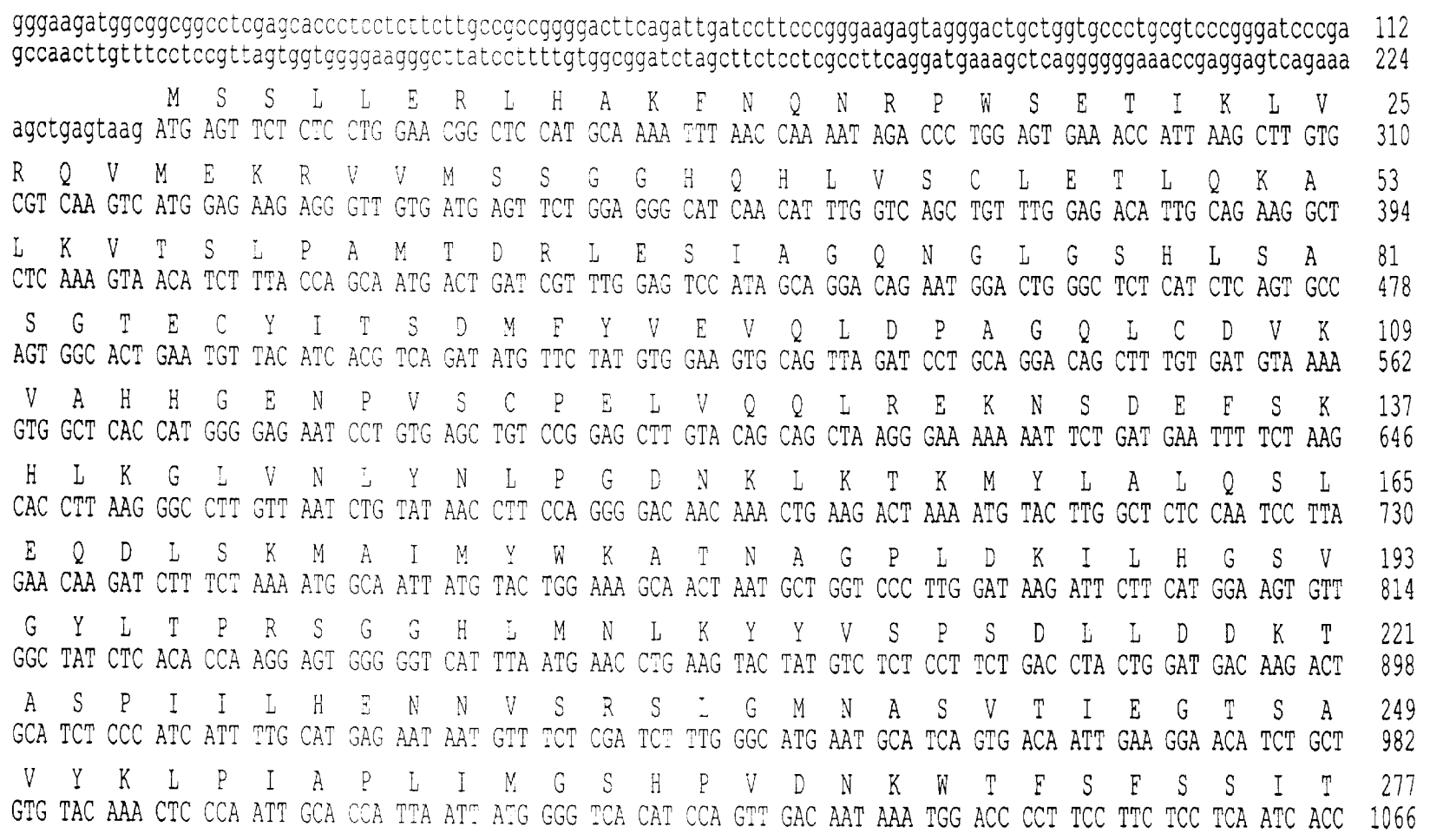
Figure 3B:
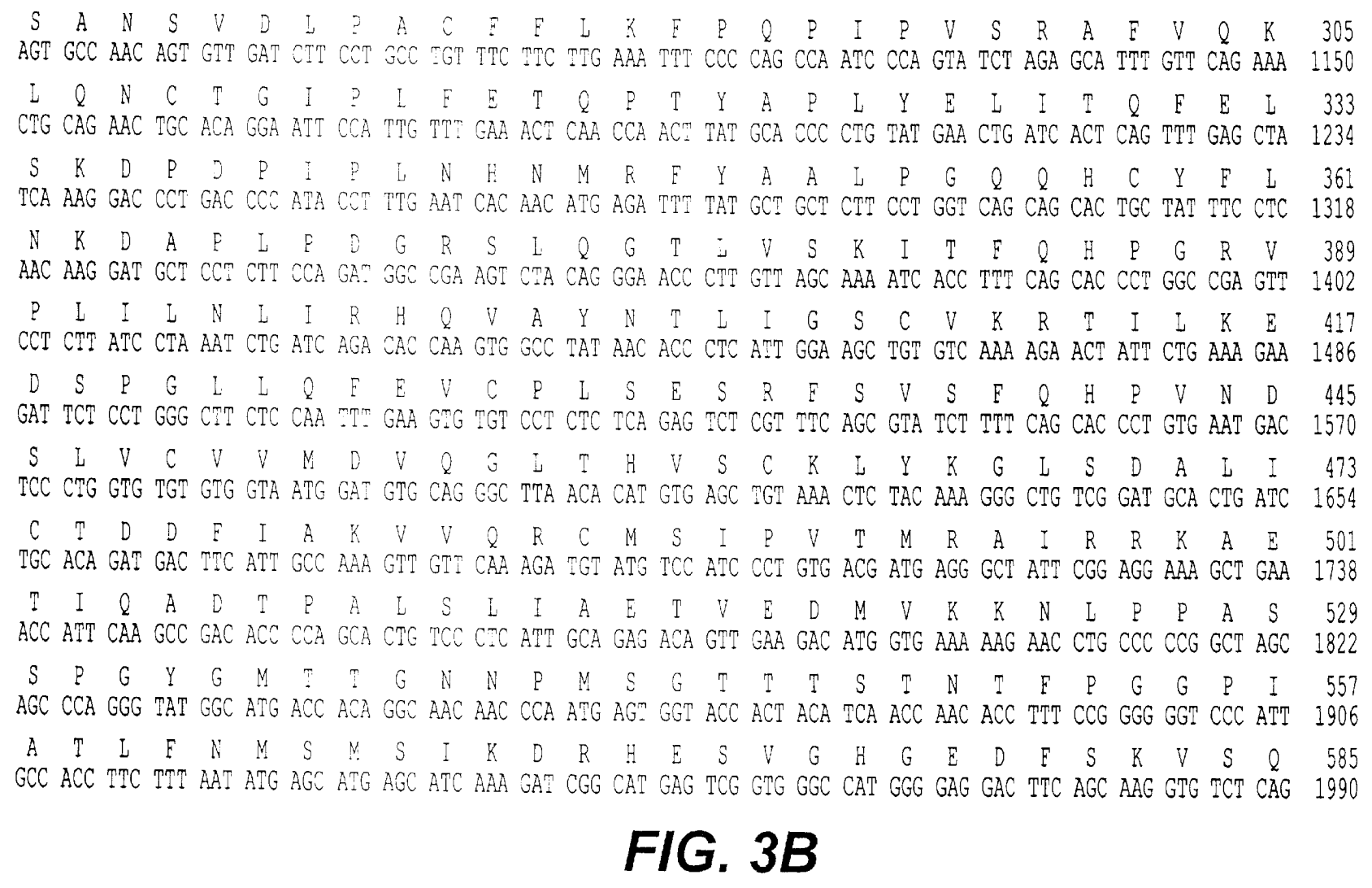
Figure 3D:
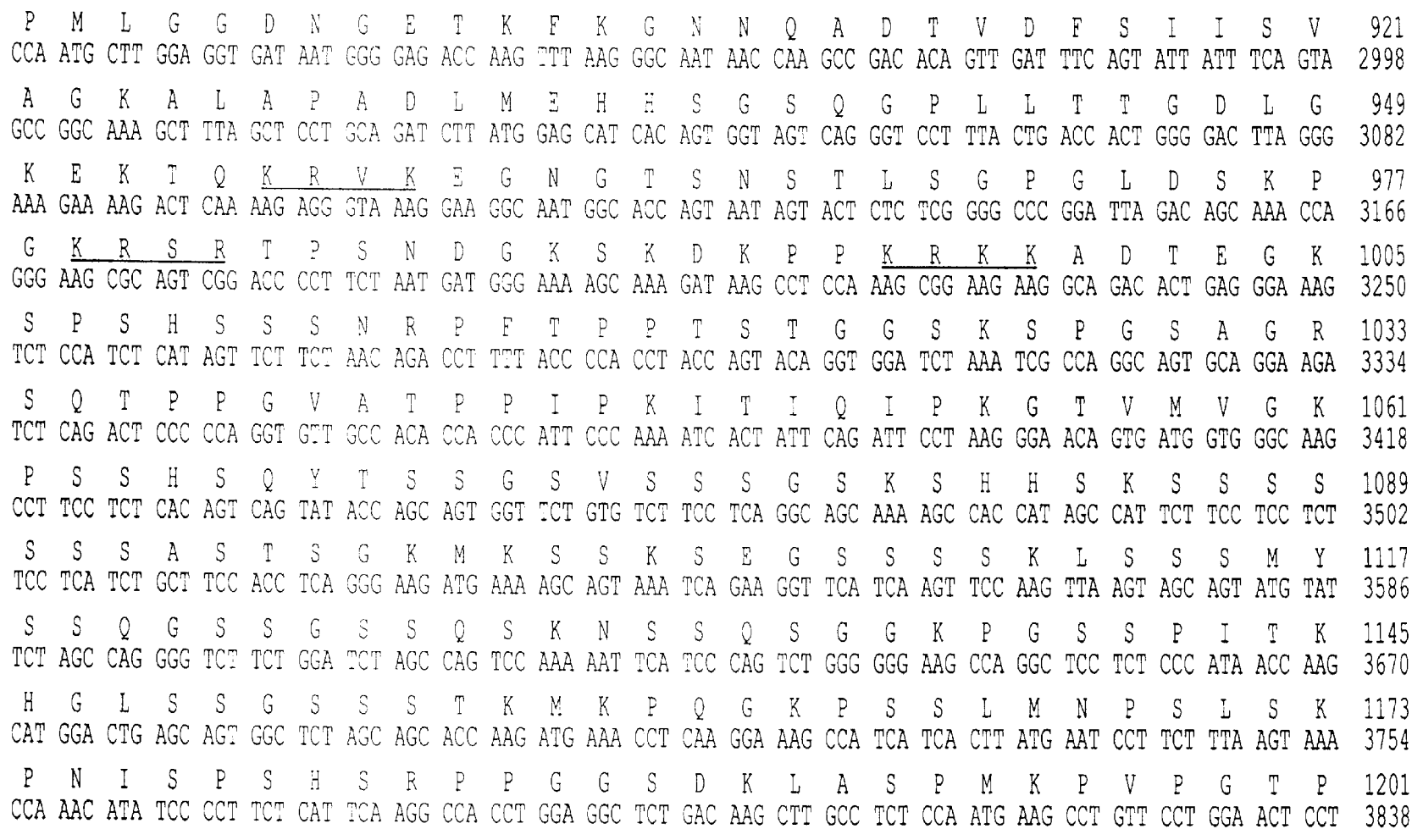
Figure 3E:
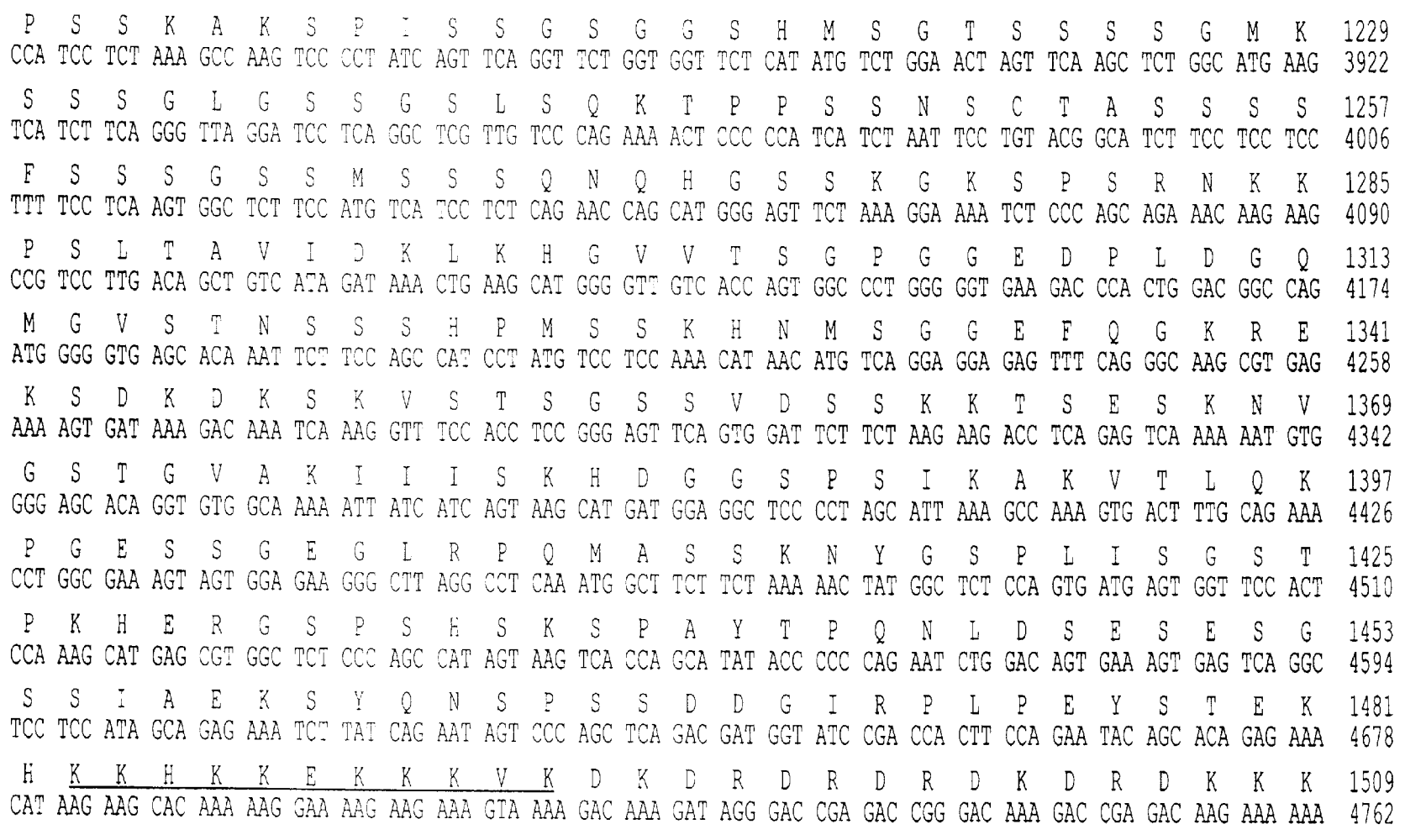

The authors of the present invention have therefore determined the sequence of the D9 cDNA. As this clone appeared to correspond to an incomplete open reading frame (FIG. 2A), a 800-base pair probe derived from the 5' end of this CDNA was generated and used in Northern blot on mRNA of various human tissues (FIG. 2B). A 8.5 kb mRNA was detected in all tissues tested except in kidney. As the highest expression was in heart, a λgt11 CDNA library from human heart was screened with the same probe used in Northern blot studies. Three clones (9.6, 9.10 and 9.1) overlapping with D9 were obtained (FIG. 2A). Sequence analysis of these cDNA clones identified a predicted open reading frame of 1566 amino acids (FIG. 3). An ATG codon was located 235 nucleotides downstream of the 5' end and was preceded by two in-frame stop codons. This ATG is probably the methionine initiation codon, since sequences immediately flanking this codon contain homology to the translation initiation sequence consensus (Kozak, 1984). A 3'-untranslated region of 877 nucleotide residues is present, but it may not contain the entire 3'-untranslated region since the polyadenylation signal is not present.

The protein encoded by this full length cDNA was named RB18A for Recognition By PAb1801 Antibody. Analysis of the amino acid sequence showed that RB18A protein contained 23.8% residues with hydroxyl side chain (17.7% serine and 6.1% threonine) and was highly charged with 13.7% basic and 17.8% acidic residues. This data also allowed to predict a 166 kDa molecular weight of RB18A protein core. However, analysis of the expression of RB18A protein in Raji cells using polyclonal antibody raised against the GST-RB18A fusion protein detected a protein with an apparent molecular weight of 205 kDa and not the p53 protein (FIG. 4). The difference between the predicted and the SDS-PAGEdetermined molecular weight is more likely due to high glycosylation and phosphorylation sites present in the protein core. Indeed, searches for structural motifs using the Prosite program revealed 13 potential N-glycosylation sites and a high number of putative phosphorylation sites (5 cAMP- and cGMP-dependent protein kinase, 29 protein Kinase C and 24 casein kinase II consensus sites). In addition, seven sequences containing the 4 aa motif Lys-Arg/Lys-X-Arg/Lys which represents the minimal nuclear localisation signal (NLS) consensus sequence could be identified (FIG. 3, underlined).

However, despite common antigenic determinants with p53, analysis of nucleotide and protein sequences in Genbank and EMBL databases did not reveal any significant homology between RB18A and p53 proteins. Interestingly, while RB18A cDNA sequence was not present in any available data bank, a region of 244 bp (corresponding to nucleotides 2054 to 2297) presented a high sequence homology with the partial sequence of Trip2 cDNA (Lee et al., 1995).

EXAMPLE 3

Binding Properties of RB18A Protein

A. Materials and Methods
GST-fusion-protein Affinity Chromatograohy

GST fusion proteins were produced in E. coli strain BL21 and purified on glutathione Sepharose 4B beads (Pharmacia LKB) as described by the manufacturer. Equal amount (1 µg) of GST-RB18A fusion proteins or GST alone bound to beads were incubated with $^{35}$S-radiolabelled translated products for 1 h at 4° C. in buffer containing 50 mM Tris (pH 7.1), 150 mM NaCl, 1 mM EDTA, and 1% NP40. After washing, pelleting, and boiling in Laemmli buffer, eluted proteins were resolved on 10% SDS/PAGE and visualized by autoradiography.
DNA-binding Assay DNA-binding assays of $^{35}$S-translated products (3 µl) or GST-fusion proteins (1 µg) were performed as previously described (Kern et al., 1991) except that GST-fusion proteins were detected by immunoblotting using a polyclonal anti-GST Ab diluted 1/500 (Oncogene Science).

B. Results

The presence of common antigenic determinants between RB18A and p53 proteins, despite the absence of significant sequence homology in their primary structure, led the authors of the present invention to analyze whether RB18A protein presented identical functions to p53 protein. Thus, properties of RB18A to bind to DNA, to homo-oligomerize and to interact with other proteins were analyzed. These studies were performed with the translated product of D9 cDNA clone. Indeed, this latter which represents part of the full length RB18A cDNA was recognized by the different anti-p53 moAb mentionned above, therefore carrying the antigenic epitopes common with p53.

First, DNA binding property of RB18A was analyzed by measuring binding of in vitro $^{35}$S-translated product on DNA-cellulose, as used for DNA-binding affinity of wild-type and mutant p53 (Kern et al., 1991). In these assays, in vitro $^{35}$S-translated product of wild-type p53 and luciferase were used as positive and negative control, respectively. In presence of the predetermined optimal 100 mM NaCl concentration (FIG. 5A), a similar yield (20% of input) of added RB18A or wild-type p53 proteins was retained on double-stranded DNA-cellulose (FIG. 5B), as well as wild-type p53 protein. In control, luciferase product did not bind to DNA-cellulose (less than 0.1% of input). Similar results were obtained using single-stranded DNA-cellulose. The interaction of in vitro translated RB18A product with DNA-cellulose was not mediated by a component of reticulocyte lysate, as identical interaction was observed with RB18A fusion protein (see FIG. 7, part D). Thus, RB18A protein is a DNA binding protein, as well as p53 protein.

Second, formation of RB18A homo-oligomers was also investigated by incubating in vitro translated product of RB18A with RB18A inserted into the pGEX4T-3 bacterial expression vector (GST-RB18A-N1). Luciferase translated products and GST were also used in control. As shown in FIG. 6, $^{35}$S-RB18A protein bound on GST-RB18A-N1, 10% of input (lane 2) but not on GST (lane 3). In control, luciferase did not bind either on GST-RB18A-N1 (lane 5) or on GST (lane 6). Thus, RB18A protein has also the property to self-oligomerize.

Third, binding properties of RB18A protein to wild-type p53 and mutant p53 273P proteins were analyzed. As shown in FIG. 6, both wild type p53 (lane 8) and mutant p53 (lane 11) bound, with an identical yield of 10% of input, on GST-RB18A and not on GST (lanes 9 and 12), respectively. Quantification of the amount of RB18A or p53 proteins retained on GST-RB18A supported a molar ratio of one to one in both cases. Thus, RB18A protein presented the property to bind to wild-type, as well as to mutant p53.

EXAMPLE 4

Mapping of Binding Domains of RB18A Protein

The domains of RB18A responsible for its binding activities were analyzed using deletion mutants of GST fusion proteins of RB18A (FIG. 7A) and by immunoblotting assays with PAb1801 and PAb421 moAbs. Data demonstrated that: a) the PAbl801 moAb binding site was localized on the last 25 residues (aa 1537 to 1566) of the RB18A C-terminal domain (FIG. 7B1); b) PAb421 moAb binding site was localized on region 927–1406 of RB18A (FIG. 7B2).

Localization of p53-binding and oligomerization domains were determined by studying the interaction of the different mutants with in vitro $^{35}$S-translated products of RB18A and p53wt cDNAs. Both p53 binding and homo-oligomerization domains were localized on the same region (between amino acids 1234 and 1406) (FIG. 7C).

DNA-binding domains were determined by incubating the different GST-fusion proteins with DNA-cellulose and by detecting bound proteins by immunoblotting with polyclonal anti-GST Ab. As shown in FIG. 7D, binding of RB18A on DNA required a domain also characterized by amino acids 927 to 1406. All the results obtained are summarized in FIG. 7E.

EXAMPLE 5

RB18A Regulates the Sequence-specific DNA Binding Function of p53

A. Materials and Methods
Electrolphoretic Mobility Shift Assay (EMSA)

The oligonucleotide containing the 20-mer p53 consensus DNA binding site and ECORI-compatible ends 5'-AATTCAGACATGCCTAGACATGCCTG-3' (SEQ ID n°9) (Funk et al., 1992) was synthesized, hybridized with the complementary oligonucleotide and end-labeled with ($^{32}$P) γ-ATP as described (Sambrook et al., 1989).

An oligonucleotide (TL; Hupp et al., 1992), 5'-TATGTCTAAGGGACCTGCGGTTGGCATTGATCTTG-3' (SEQ ID n°10), which did not contain the consensus sequence was prepared in double-stranded form and used as non-specific competitor.

EMSA was performed as follows. Translated product (4 µl) was pre-incubated for 20 min at room temperature with 1 µg of GST-RB18A fusion protein or 0.2 µg of moAb in a final reaction volume of 14 µl of buffer A (25 mM Tris, pH 7.4, 80 mM KCl, 0.1 mM EDTA, 1 mM DTT and 10% glycerol). Then, 6 µl of buffer B (80 mM KCl, 16.6 mM $MgCl_2$ and 3 mg/ml BSA) containing 0.4 ng of labeled oligonucleotide and 0.5 µg of poly(dI-dC) were added and incubation was carried out for 20 min at 4° C. Reaction products were run for 15 min at 200 V on a 4% polyacrylamide gel containing 0.4×Tris-Borate-EDTA (90 mM Tris, 64.6 mM Borate, 2.5 mM EDTA, pH 8.3).

B. Results

Binding property of RB18A on p53 led the authors of the present invention to analyze whether RB18A could regulate p53 specific binding on the DNA consensus binding site (Funk et al., 1992). For this purpose, the electrophoretic mobility shift assay (EMSA) was used (FIG. 8, Part A), as described by Wolkowicz et al. (1995). This assay allowed to demontrate that in vitro translated product of wild type p53, bound specifically to DNA only when activated by PAb421 (lane 5) but not in non activated state (lane 2) or when incubated with PAb1801 (lane 6). In these conditions, while C-terminal GST-RB18A fusion protein (GST-RB18A-N2) did not interact directly with the specific p53 oligonucleotide (lane 4), its addition induced the binding of p53 to its specific oligonucleotide (lane 7). Identical results were obtained using GST-RB18A-NC2. The specificity of this binding was supported by its inhibition in presence of 50 fold molar excess of unlabelled p53 specific oligonucleotide (lane 8) and not by a non specific oligonucleotide (lane 9). Activation of p53 DNA binding activity by RB18A was not detected when the GST-RB18A-NI1 mutant, deleted in its p53-binding domain, was used instead of the GST-RB18A-N2 fusion protein (lane 10), suggesting that this activation needed the interaction of both proteins.

Analysis of the components present in the specific DNA-binding complex was performed using either anti-p53 moAbs, polyclonal anti-GST Ab or anti-RB18A Ab. As shown in FIG. 8, Part B, the formed complex (lane 2) was supershifted in presence of anti-p53 moAbs as PAb421 (lane 3), PAb1801 (lane 4) or DO-1 (lane 5) but neither by anti-RB18A Abs (lane 6) nor by anti-GST. In addition, RB18A synergized the activation of p53 by PAb421 (FIG. 9), in a dose-dependent manner, whether added before (lanes 6 to 8) or after (lanes 1 to 4) the Moab. In control, the RB18A mutant which lost its binding domain with p53 did not have the same effect (lanes 5 or 9). Altogether, these data supported that RB18A activated p53 DNA-binding activity, while not present in the observed complex.

EXEMPLE 6

The Carboxy-terminal Domain of RB18A Induces a Dose Dependent Reassociation of DNA Double Strands, as Well as Wild-type p53

Figure 10A:
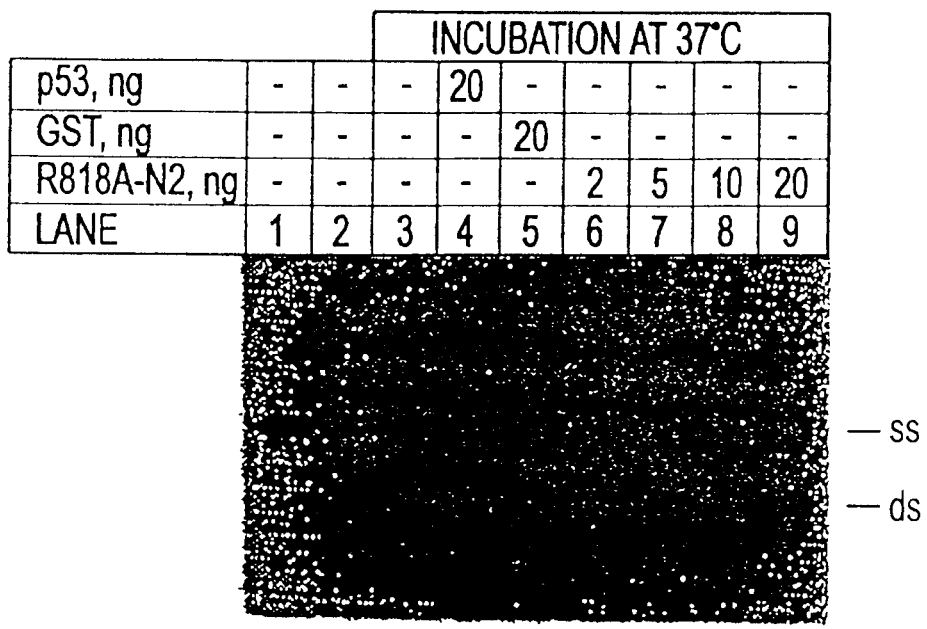
Figure 10B:
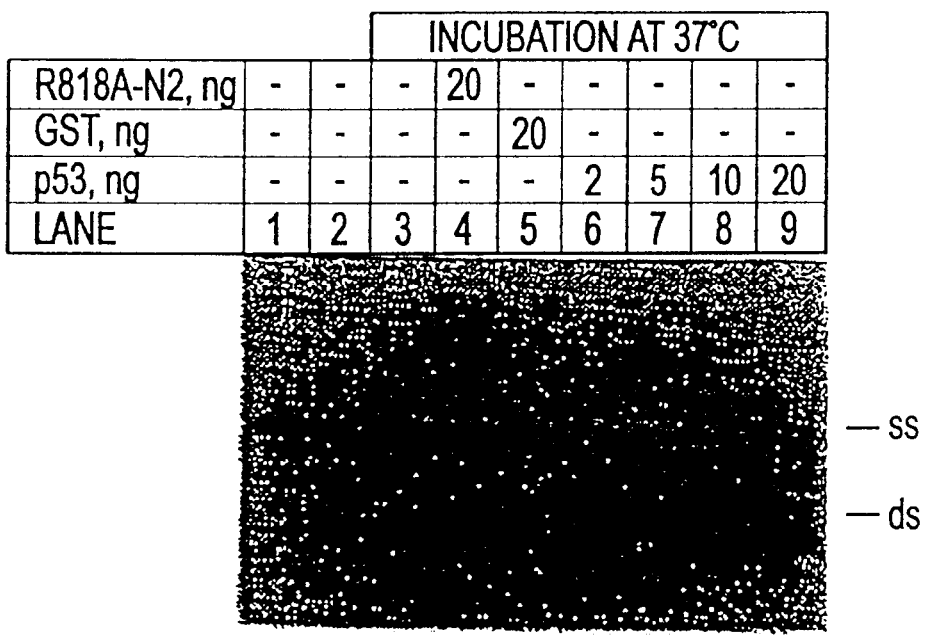

In order to analyze whether the domain recognized by PAb421 moAb on RB18A could also present a DNA renaturation activity, the 194 bp fragment obtained after digestion of the φx174 phage DNA by the restriction enzyme HaeIII was used (FIGS. 10A and 10B). GST fusion protein corresponding to the carboxy-terminal domain of RB18A (GST-RB18A-N2; aa 1234–1566) was prepared as in example 1. This fusion protein contains the DNA binding domain, the oligomerization domain and also the domain responsible for interaction with p53. The recombinant human wild-type p53 was purified from E. coli using metal chelate chromatography as described by Midgley et al. (1992). DNA fragment was end-radiolabeled, heat denaturated, and incubated with wild-type p53 or RB18A recombinant proteins. In presence of GST-RB18A-N2 (FIG. 10A) or recombinant p53 (FIG. 10B), a dose-dependant reassociation of DNA strands was observed. In absence of protein (lanes 3) or in presence of GST (lanes 5), DNA annealing was undetectable even after 25 min at 37° C. FIG. 11 shows the time course of DNA renaturation by carboxy-terminal domain of RB18A or wild-type p53 at a protein concentration of 20 nM. The initial rate was 14% per min for GST-RB18A-N2. The initial rate found for wild-type p53 was 5.9% per min, consistent with the value obtained by others (Wu et al., 1995).

It is well known that basic proteins enhance the DNA renaturation by neutralizing the charge of the phosphate backbone of the nucleic acids. Given that both carboxy-terminal domain of RB18A and p53 are basic, basic chicken lysozyme (pHi 11.0) was used as control and the DNA renaturation rate initiated by this protein was compared to those initiated by RB18A or p53. Even at a concentration of 500 nM, lysozyme had a minimal effect on DNA annealing. This result demonstrated that the DNA renaturation activity associated with RB18A (and p53) was not due only to their basic biochemical nature but was functionally significant.

The fact that RB18A was able to form homo-oligomer suggests that each molecule of a RB18A dimer could promote the duplex formation.

EXAMPLE 7

The Carboxy-terminal Domain of RB18A in vitro Stimulates the Sequence-specific DNA Binding of Wild-type p53, but does not Affect Properties of Mutated p53

Recently, Selivanova et al. (1997) demonstrated that a peptide derived from the PAb421 epitope of p53 was able to stimulate in vivo the transactivation activity of wild-type and mutated p53. As RB18A also presented this epitope in its carboxy-terminal domain, the authors of the present invention tested whether carboxy-terminal domain of RB18A was also able to activate in vitro the sequence-specific DNA binding of various mutated forms of p53. For this purpose, 3 different p53 mutants were used: p53-175H, p53-179Q and p53-273P. The results obtained are presented in FIG. 12B. As previously demonstrated, RB18A (lane 3) and PAb421 moAb (lane 2) were able to stimulate the specific binding of wild-type p53 (lane 1). However, neither PAb421 moAb, nor GST-RB18A-N2 were able to activate the DNA binding function of p53-175H (lanes 5 and 6, respectively) or p53-179Q (lanes 8 and 9, respectively), although these proteins were efficiently translated (FIG. 12A). Same results were obtained with p53-273P. Rolley et al. (1995), have also demonstrated that PAb421 moAb could not activate the DNA specific binding of p53-175H and p53-273P. These results suggest that RB18A is not able to restitute the correct conformation of the sequence-specific DNA binding domain of p53 mutants. Moreover, this suggests that RB18A does not activate wild-type p53 by stabilizing the conformation of its core domain, but rather by inhibiting the negative effect of its C-terminal regulatory domain.

EXAMPLE 8

The Carboxy-terminal Domain of RB18A in vivo can Functionally Interact and Stimulates the Transactivation Activity of wt p53 but not Mutated p53

Figure 13B:
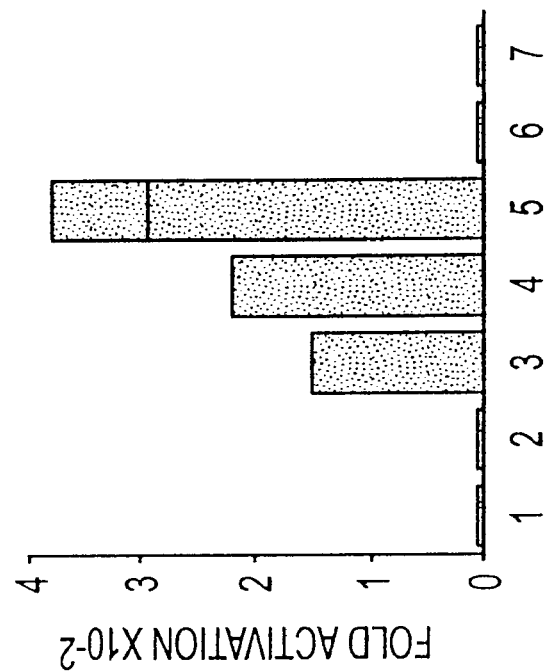
Figure 13A:
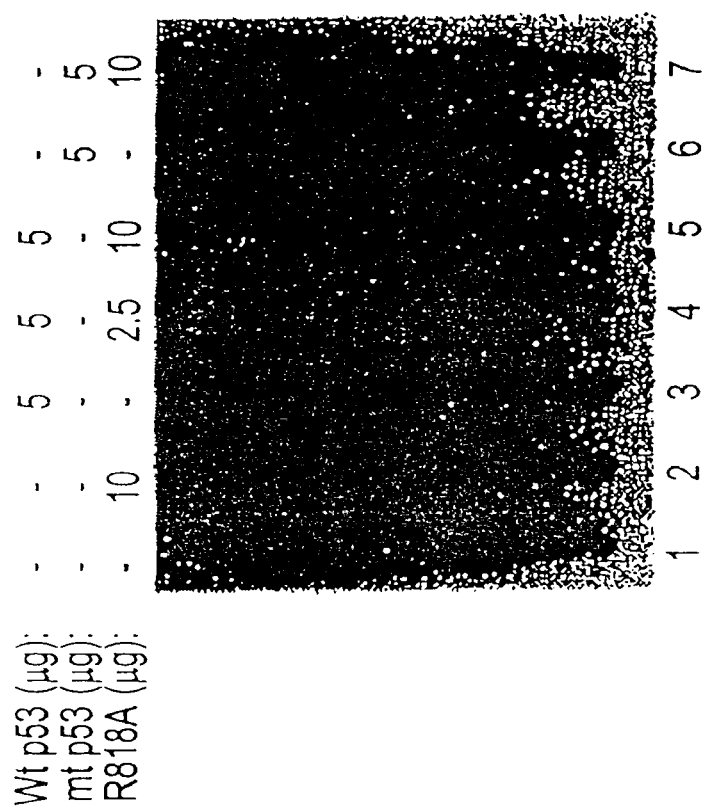

A. The authors of the present invention have tested the ability of the carboxy-terminal domain of RB18A to stimulate the transactivation activity of wild-type and mutated p53 in vivo. They used a construction containing the CAT gene cloned downstream 13 repeats of PG, the DNA consensus-binding site for p53 (Funk et al., 1992). K562 cells were used for transfection as they are p53 deficient (Law et al., 1993). As shown in FIG. 13, the carboxy-terminal domain of RB18A stimulated the transactivation activity of wild-type p53 in a dose-ependent manner. Indeed, a 1.5 to 3 fold activation was observed when the ratio of RB18A to p53 was 0.5 to 2 (lanes 4 and 5, respectively). These results are the first evidence that carboxy-terminal domain of RB18A can functionally interact in vivo with wild-type p53. At the opposite, no CAT activity was observed in cells transfected with p53-175H alone (lane 6) or in combination with the carboxy-terminal domain of RB18A (lane 7). Other mutated p53 as p53-179Q were also tested but no stimulation was observed. Therefore, the results obtained in vivo are consistent with those obtained in vitro, that RB18A was able to stimulate the transactivation only by wild-type and not mutated p53.

B. H1299 and K562 cells were used for transfection as they are p53 deficient. These cells were transfected with cDNA of RB18A and wild-type p53, in association with promoters that include response elements to p53.

These promoters were inserted upstream to a reporter gene such as CAT or luciferase. The tested promoters were:

$p21^{Waf1}$ which is involved in controlling the passage from the $G_1$ phase to the S phase in the cell cycle, along with the cyclin/CDK complex;

MDM2 which induces the degradation of p53 by proteasome;

IGF~BP3 which prevents the fixation of IGF on its receptor, blocking its mitotic action and as a result inducing cell apoptosis.

The obtained results show that co-expressing the C-terminal domain of RB18A with p53 leads to a 5-fold-stimulation of the activation of MDM2, a 10-fold-stimulation of the activation of $p21^{Waf1}$ and a 13-fold-stimulation of IGF~BP3.

EXAMPLE 9

RB18A in vivo can Transactivate Certain Physiological Promoters Independently from p53

By carrying out the experiments of example 8B, the authors of the present invention showed that RB18A can transactivate, independently from p53, the activity of IGF~BP3 promotor (10-fold-stimulation). As a control, RB18A alone has no significant effect on $p21^{Waf1}$ and MDM2 promoters.

EXAMPLE 10

RB18A Inhibits p53-induced-apoptosis

K562 cells from an erythroleukemia line deficient for p53 were cotransfected with cDNA coding for the C-terminal domain of RB18A and CDNA coding for wild-type p53.

Apoptosis was evaluated by Flow Cytometry Analysis, by using propidium iodide and determining the percentage of apoptotic cells expressing p53.

These measures showed that the expression of RB18A inhibits the p53-induced apoptosis. This inhibition is detectable after 48 hours after transfecting and reaches 50% after 72 hours.

This inhibition of p53-induced apoptosis, along with the transactivation of IGF~BP3 which on the contrary induces apoptosis, supports that RB18A exhibits a regulatory property on cell growth.

REFERENCES

Arrowsmith C H and Morin P. (1996). *Oncoaene*, 12, 1379–1385.

Barak Y, Juven T, Haffner R and Oren M. (1993). *EMBO J.*, 12, 461–468.

Barel M, Fiandino A, Lyamani F and Frade R. (1989). *Proc. Natl. Acad. Sci. USA*, 86, 10054–10058.

Barel M, Gauffre A, Lyamani F, Fiandino A, Hermann J and Frade R. (1991). *J. Immunol.*, 147, 1286–1291.

Bargonetti J, Manfredi J J, Chen X, Marshak D R and Prives C. (1993). *Genes Dev.*, 7, 2565–2574.

Cox L S, Hupp T, Midgley C A and Lane D P. (1995). *EMBO J.*, 14, 2099–2105.

Daud A I, Lanson N A, Claycomb W C and Field L J. (1993). *Am. J. Physiol.*, 264, H1693–H1700.

El-Deiry W S, Kern S E, Pietenpol J A, Kinzler K W and Vogelstein B. (1992). *Nature Genet.*, 1, 45–49.

El-Deiry W S, Tokino T, Velculescu V E, Levy D B, Parsons R, Trent J M, Lin D, Mercer E., Kinzler K W and Vogelstein B. (1993). *Cell*, 75, 817–825.

Fields S and Jang S K. (1990). *Science*, 249, 1046–1049.

Ford M J, Anton I A and Lane D P. (1988). *Nature*, 332, 736–738.

Fritsche M, Haessler C and Brandner G. (1993). *Oncoaene*, 8, 307–318.

Funk W D, Pak D T, Karas R H, Wright W E and Shay J W. (1992). *Mol. Cell Biol.*, 12, 2866–2871.

Gannon J V, Greaves R, lggo R and Lane D P. (1990). *EMBO J.*, 9, 1595–1602.

Geysen H M, Rodda S J and Mason T J. (1986). *Mol. Immunol.*, 23, 709–715.

Geysen H M, Rodda S J, Mason T J, Tribbick G and Schoofs P G. (1987). *J. Immunol. Methods*, 102, 259–274.

Ginsberg D, Michael-Michalovitz D, Ginsberg D and Oren M. (1991). *Mol. Cell. Biol.*, 11, 582–585.

Harris N, Brill E, Shohat O, Prokocimer M, Wolf D, Arai N and Rotter V. (1986). *Mol. Cell Biol.*, 6, 4650–4656.

Hirling H, Scheffner M, Restle T and Stahl H. (1989). *Nature*, 339, 562–564.

Hupp T R, Meek D W, Midgley C A and Lane D P. (1992). *Cell*, 71, 875–886.

Hupp T R, Sparks A and Lane D P. (1995). *Cell.* 83, 237–245.

Jayaraman L and Prives C. (1995). *Cell*, 81, 1021–1029.

Johnson P, Chung S and Benchimol S. (1993). *Mol. Cell. Biol.*, 13, 1456–1463.

Kastan M B, Onyekwere O, Sidransky D, Vogelstein B and Craig R W. (1991). *Cancer Res.*, 51, 6304–6311.

Kastan M B, Zhan Q, EI-Deyri W S, Carrier F, Jacks T, Walsh W V, Plunkett B S,

Vogelstein B and Fornace Jr A L. (1992). *Cell*, 71, 587–597.

Kern S E, Kinzler K W, Baker S J, Nigro J M, Rotter V, Levine A J, Friedman P,

Prives P and Vogelstein B. (1991). *Oncogene*, 6, 131–136.

Kim K K, Daud A I, Wong S C, Pajak L, Tsai S-C, Wang H, Henzel W J and Field L J. (1996). *J. Biol. Chem.*, 46, 29255–29264.

Kozak M. (1984). *Nucleic Acids Res.*, 12, 857–872.
Laempli U K. (1970). *Nature*, 227, 680–685.
Lane D P and Crawford L V. (1979). *Nature*, 278, 261–263.
Lane D P and Hoeffler W K. (1980). *Nature*, 288,167–170.
Lane D P. (1992). *Nature*, 358,15–16.
Law et al., (1993).
Lee J W, Choi H S, Gyuris J, Brent R and Moore D D. (1995). *Mol. Endocrinol.*, 9, 243–254.
Legros Y, Lafon C and Soussi T. (1994). *Oncogene*, 9, 2071–2076.
Maheswaran S, Park S, Bernard A, Morris J F, Rauscher III F J, Hill D E and Haber D A. (1993). *Proc. Natl. Acad. Sci. USA*, 90, 5100–5104.
Mercer W E, Shields M T, Lin D, Appella E and Ullrich S J. (1991). *Proc. Natl. Acad. Sci. USA*, 88, 1958–1962.
Midgley et al., (1992), *J. Cell Sci., USA*, 101, 183–189.
Miller S D, Farmer G and Prives C. (1995). *Mol. Cell Biol.*, 15, 6554–6560.
Milne D M, McKendrick L, Jardine L J, Deacon E, Lord, J M and Meek D W. (1996). *Oncogene*, 13, 205–211.
Milner J, Cook A and Sheldon M. (1987). *Oncopene*, 1, 453–455.
Mommand J, Zambetti G P, Olson D C, George D and Levine A J. (1992). *Cell*, 69, 1237–1245.
O'Rourke R W, Miller C W, Kato G K, Simon K J, Chen D L, Dang C V and Koeffler H P. (1990). *Oncogene*, 5, 1829–1832.
Pavletich N P, Chambers K A and Pabo C O. (1993). *Genes Dev.*, 7, 2556–2564.
Pinhasi-Kimhi O, Michalovitz D, Ben-Ze'ev A J and Oren M. (1986). *Nature*, 320, 182–185.
Radinsky R. Fidler I J, Price J E, Esumi N. Tsan R. Petty C M, Bucana C D and Bar-Eli M. (1994). *Oncogene*, 9, 1877–1883.
Raycroft L, Wu H and Lozano G. (1990). *Science*, 249, 1049–1051.
Raymond W E and Kleckner N. (1993). *Nucleic Acids Res.*, 21, 3851–3856.
Reed M, Woelker B, Wang P, Wang Y, Anderson M E and Tegtmeyer P. (1995). *Proc. Natl. Acad. Sci. USA*, 92, 9455–9459.
Rolley et al., (1995), *Oncogene*, 11, 763–770.
Sambrook J, Fritsch E F and Maniatis T. (1989). *Molecular cloning: A laboratory Manual.* 2nd Ed., Cold Spring Harbor Laboratory, Cold Spring Harbor, N.Y.
Santhanam U, Ray A and Sehgal P B. (1991). *Proc. Natl. Acad. Sci. USA*, 88, 7605–7609.
Sarnow P, H O Y S, Williams J and Levine A J. (1982). *Cell*, 28, 387–394.
Scharer E and Iggo R. (1992). *Nucleic Acids Res.*, 20, 1539–1545.
Selivanova et al., (1997), *Nature Med.*, 3, 405–413.
Seto E, Usheva A, Zambetti G P, Mommand J, Horikoshi N, Weinmann R, Levine A J and Shenk T. (1992). *Proc. Natl. Acad. Sci. USA*, 89, 12028–12032.
Shaw P, Bovey R, Tardy S, Sahli R, Sordat B and Costa J. (1992). *Proc. Natl. Acad. Sci. USA*, 89, 4495–4499.
Simons A, Melamed-Bessudo C, Wolkowicz R, Sperling J, Sperling R, Eisenbach L and Rotter V. (1997). *Oncoaene*, 14, 145–155.
Soussi T, Caron de Fromentel C and May P. (1990). *Oncogene*, 5, 945–952.
Stephen C W, Helminen P and Lane D P. (1995). *J. Mol. Biol.*, 248, 58–78.
Subler M, Martin D and Deb S. (1992). *J. Virol.*, 66, 4757–4762.
Takenaka I, Morin F. Seizinger B R and Kley N. (1995). *J. Biol. Chem.*, 270, 5405–5411.
Wang Y. Reed M, Wang P, Stenger J E, Mayr G. Anderson M E, Schwedes J F and Tegtmeyer P. (1993). *Genes Dev.*, 7, 2575–2586.
Weintraub H, Hauschka S and Tapscott S J. (1991). *Proc. Natl. Acad. Sci. USA*, 88, 4570–4574.
Wolkowicz R. Peled A, Elkind N B and Rotter V. (1995). *Proc. Natl. Acad. Sci. USA*, 92, 6842–6846.
Wu et al., (1995), *Mol. Cell. Biol.*, 15, 497–504.
Yonish-Rouach E, Resnitsky D, Lotem J, Sachs L, Kimchi A and Oren M. (1991). *Nature*, 352, 345–347.
Zhang Q, Gutsch D and Kenney S. (1994). *Mol. Cell Biol.*, 14, 1929–1938.

What is claimed is:

1. An isolated RB18A polypeptide having the amino acid sequence of SEQ ID No. 2.

2. An isolated polypeptide comprising a sequence selected from the group consisting of a fragment from amino acid 436 to amino acid 1566 of SEQ ID No. 2, a fragment from amino acid 436 to amino acid 1228 of SEQ ID No. 2, a fragment from amino acid 436 to amino acid 927 of SEQ ID No. 2, a fragment from amino acid 1537 to amino acid 1566 of SEQ ID No. 2, a fragment from amino acid 1234 to amino acid 1566 of SEQ ID No. 2, a fragment from amino acid 1234 to amino acid 1406 of SEQ ID No. 2, a fragment from amino acid 927 to amino acid 1406 of SEQ ID No. 2.

3. An isolated polypeptide having an amino acid sequence that:

differs from SEQ ID No. 2 only by substitution of one or more amino acids;

shows at least 90% identity with SEQ ID No. 2; and exhibits substantially the same biological property as a polypeptide of SEQ ID No. 2, with regard to DNA binding, homooligomerization, binding to p53 and/or activation of a sequence specific DNA binding function of p53.

* * * * *